(12) United States Patent
Juo et al.

(10) Patent No.: US 9,670,489 B2
(45) Date of Patent: Jun. 6, 2017

(54) METHOD FOR TREATING AND/OR PREVENTING MYOPIA

(71) Applicant: KAOHSIUNG MEDICAL UNIVERSITY, Kaohsiung (TW)

(72) Inventors: Suh-Hang Juo, Kaohsiung (TW); Ku-Chung Chen, Kaohsiung (TW); Edward Hsi, Kaohsiung (TW); Chung-Ling Liang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 14/674,786

(22) Filed: Mar. 31, 2015

(65) Prior Publication Data
US 2016/0010087 A1    Jan. 14, 2016

Related U.S. Application Data

(60) Provisional application No. 62/024,078, filed on Jul. 14, 2014.

(51) Int. Cl.
| | |
|---|---|
| *A61K 48/00* | (2006.01) |
| *C07H 21/02* | (2006.01) |
| *C07H 21/04* | (2006.01) |
| *C12N 15/113* | (2010.01) |
| *A61K 31/713* | (2006.01) |
| *A61K 9/00* | (2006.01) |
| *A61K 9/127* | (2006.01) |

(52) U.S. Cl.
CPC .......... *C12N 15/113* (2013.01); *A61K 9/0048* (2013.01); *A61K 9/127* (2013.01); *A61K 31/713* (2013.01); *C12N 2310/113* (2013.01); *C12N 2310/14* (2013.01); *C12N 2310/141* (2013.01); *C12N 2310/3231* (2013.01); *C12N 2310/3233* (2013.01); *C12N 2320/30* (2013.01)

(58) Field of Classification Search
CPC ........................... A61K 48/00; C12N 2310/11
See application file for complete search history.

(56) References Cited

U.S. PATENT DOCUMENTS

| 7,893,302 B2* | 2/2011 | Chen ................ A61K 9/1271 435/458 |
| 2012/0288476 A1* | 11/2012 | Hartmann ......... A61K 31/7105 424/85.4 |

OTHER PUBLICATIONS

Ku-Chung Chen, et al., "MicroRNA-328 May Influence Myopia Development by Mediating the PAX6 Gene", *Investigative Ophthalmology & Visual Science*, May 2012, vol. 53, No. 6, pp. 2732-2739.

Chung-Ling Liang, et al., "A Functional Polymorphism at 3 UTR of the PAX6 Gene May Confer Risk for Extreme Myopia in the Chinese", *Investigative Ophthalmology & Visual Science*, May 2011, vol. 52, No. 6, pp. 3500-3505.

* cited by examiner

*Primary Examiner* — Amy Bowman
(74) *Attorney, Agent, or Firm* — Muncy, Geissler, Olds & Lowe, P.C.

(57) ABSTRACT

The present disclosure provides a method for treating and/or preventing myopia, including: administering an RNA interference (RNAi) to a subject, wherein the RNA interference is capable of counteracting another RNA interference, and the other RNA interference is an RNA interference capable of inhibiting an expression of PAX-6 gene, and the RNA interference capable of inhibiting an expression of PAX-6 gene comprises microRNA-328.

7 Claims, 24 Drawing Sheets

PAX6 3'UTR (SEQ ID NO. 31)  5' AGGGAACUGUCAGAGAAGGGCUAU 3'
                               | ||| || |||||  ||  :|
miR-328 (SEQ ID NO. 3)       3' UGCCUU–CCGUCUC–UCCCGGUC 5'

PAX6 3'UTR mutant (SEQ ID NO. 32) 5' AGGGAACUGUCAGAGACUUUAGCU 3'

FIG. 2A

SEQUENCE LISTING

<160> NUMBER OF SEQ ID NOS: 32

<210> SEQ ID NO 1
<211> LENGTH: 33170
<212> TYPE: DNA
<213> ORGANISM: Homo sapiens

<400> SEQUENCE: 1

```
accctctttt cttatcattg acatttaaac tctggggcag gtcctcgcgt agaacgcggc      60
tgtcagatct gccacttccc ctgccgagcg gcggtgagaa gtgtgggaac cggcgctgcc     120
aggctcacct gcctccccgc cctccgctcc caggtaaccg cccgggctcc ggccccggcc     180
cggctcgggg cccgcggggc ctctccgctg ccagcgactg ctgtccccaa atcaaagccc     240
gccccaagtg gccccggggc ttgattttg cttttaaaag gaggcataca aagatggaag     300
cgagttactg agggagggat aggaaggggg gtggaggagg gacttgtctt tgccgagtgt     360
gctcttctgc aaaagtagca aaatgttcca ctcctaagag tggacttcca gtccggccct     420
gagctgggag taggggcgg gagtctgctg ctgctgtctg ctaaagccac tcgcgaccgc     480
gaaaaatgca ggaggtgggg acgcactttg catccagacc tcctctgcat cgcagttcac     540
gacatccacg cttgggaaag tccgtacccg cgcctggagc gcttaaagac accctgccgc     600
gggtcgggcg aggtgcagca gaagtttccc gcggttgcaa agtgcagatg gctggaccgc     660
aacaaagtct agagatgggg ttcgtttctc agaaagacgc ggagtacgaa agaatgcggc     720
cgacagagct gggcagcgcg taaagctccc agcgtgtgat ttgagcttca cttcggaaga     780
cctaataatt agcgattctc actgagctag aacgcgggct ccggttactg cgggcgctgc     840
gctggctgcc tcggcgggaa gcgcgcgggc gccatgggag ccgggccgcc aagcccggga     900
aagagaagcg cccaccaccc tgcggccctt ggagggccag agccggggcc cggaagtgtc     960
cccttagtga gtcaggaag ggacgaccca aacttagact aacttgtggt tcagcccggc    1020
gaaagtcctg ggagcccggc cctaaaagca gctggagacg cccaggccgg cttaggcggg    1080
gcacccaaga acccgcccg ggagtttggg gcggcctctg ggccaggccc cggctagccc    1140
ccaaccccca ctcccactcg cgctcctgcg ccccctttct aggtcttctg ggagcacctt    1200
cggagctcag tcacctgtga caggtgttgg gacctccgcc cgactccgag cggtggcgcc    1260
ccctgctcac ctcacctgga aacggggggac gagcgcagtg gcagtccggc cgcacgcctt    1320
acctgggccg ggatcctctc ctccgcgggt tcctctccct ggagctgggc ggcgagcagg    1380
tcgcctgctt cgcagtggga agtggacctt ctcctccagt cataaatcaa acccagccat    1440
cctcgggcct cctccctcat tagagatgtt tattggagat cgtgtttatt cggctgtcac    1500
ggcgagaaaa cgcggtgaca taattacctc tgaccagagt cctcgctccg cgcccagggc    1560
gagccgagga cctcctctgt cgccttctca tgcccgtgcc cttcgtgatc ggagggcgcc    1620
cgtgataggc ttgtcttttt ttcctcagac cctctcatag aatttggatg actggaatta    1680
ctattcagat ttccccaggg cccggagttt atttattat tttagaattg gaaaggaaaa    1740
```

-continued

```
ccgaagggaa cccaacgccc ctccggggca gaaggggca gcgcgcgcga ggcggaagga      1800
cagtcactct cgctgcacaa actttcccgc gggccgcgcc gcgcgtgcag gggctggacg      1860
ccacccggcg ccagagccgg gcctgaggag cggggtctgg ccgggaacga gggctgccag      1920
cctgggtggt gtcatttgtt gcttcatttt tcattccctt tcctctcgtg aggaatcaga      1980
ggcatcgggc cgcgcgggct gagaattctt aaattctccc cggccgcatt cggctgagcc      2040
aacccgcagt tcctgtcagc ccctctgtcc cccgggcagc ggttttcccc gctagccagg      2100
tttggaagtc accctctgtg agactgggtt aggaagtgac gaaaagcgcc gaattgtttt      2160
caaattgaaa atactttttt ttttttttt ggagatagcg ctgacaaata tatgggatcc      2220
cggcttttga tccctggctg ccgcctctgt tctcctgtcg ctaataaaac tcgcattgag      2280
ccccttagtg ccttgattaa caggcagatt aactcttact ggggttggga acagcttgtc      2340
ctaatcaatg tcattttaaa agcccgtcag gatgcgctta gcttcggttc cctggatgct      2400
tgagcgagcc agccatgaca tttgctccct cccctcccc agcctcaaat ccccagtaa      2460
agcccccagt tcccgcctgc ctgttcccag gtctacaacg ggacaaatcg caggaccggg      2520
tcgttggcct ttagaatagg cagcggttta gagagggat atccaggag aagggactga      2580
ggtggccttg acttgcttgc ttttcctttg aagctgaact cttgcctctt gggggcagag      2640
gttacaggga aaagagagat ggggggatcg tcacagggtg atgaaatgga aagcaaactt      2700
ttctaggaac cctatttgca aaaatcggag agtgccgctg atttcagttg tcctacatgt      2760
caggagtttt aaacctaact cctatctgga caacagcatg gagggactgg gaggcaaagc      2820
cttgggagtc tgacccgctg ggctgctagg aatcccttg ctgggagact ccactggaca      2880
atgttatttt aaaggtattt tggggtggg cagggagaag acagagagag aaagagagag      2940
agagagagag agagagagag agagagagag acaggctggc ctcccagagc gaacggaaga      3000
ggactgagga ctgaacccag ggagccccta gcactggcca tttggcagga ggcgaggaag      3060
ggcgagggca ccgcggcttc cccccaagcc gagcagtggc cacagcctga aggtgccacg      3120
gggcggctct gggatcttct tggcttttct aggctctggg ctcggcgagg ctgccgggtt      3180
agcgggaacc ggcaggttgc tggagaaagg agagggacaa aggcctggaa gtgggggagg      3240
caccagggac tgggcggccg ggatgggagc ctttgccttt agggctcact ggacccgttt      3300
gccagctccg cggacaaggg atcccacctt cccaggtgtct gcaaaaagag agacgtttgg      3360
ggcactacaa agtgacgcag gtgtctgcca agactttcct tctccaaaaa atgccagtct      3420
tcacccttc cagcgcgccg gcgctgcgcc tctgcttgac cggggaaaga gagagtttgg      3480
aggtgtcaga actgtcagaa ctccggatgg gaggctcttg gttctgaagc tgggagctgg      3540
aggcacttcc ccccagaagt gggcacttct ttgcctcccc gaaggcctga tggggtgggc      3600
acagggaat gccagggatc ggtgcgggtg agatgcttgc ctcacctcat gttgacgcat      3660
caatactggc tagaagctct gggcaggctc tggcagcca cggtccccca gcgggactcc      3720
ctccacgcag acagccccgc taccgggtgg gacgaccccg cgcggccccg cgggaacgca      3780
cccgccggcc tgagaggtcc tccctctggc cacaggggc ggagggtagg ggggaacagg      3840
ggcctgtggg gaggcgggga aaggagacag aacctaaagc gcaatccccg ccgcccccc      3900
gcgtcttgga gggcagcaag tgggcctcgg gcgtgttggt agccgcaatt aaaatggcga      3960
cctgcgagtt gtctcggttt tgtacacacc tctggcaacc gcgcccgcac ctcagtctcg      4020
gcccccacac ccctaggccg cttcgccccc agagccggta cttggcagag ggagtgaggc      4080
tccccacgag gtagaacagc accccacct tccttgagac cagtccagag agaacgagga      4140
```

```
aatctcactc tcaccectct ctccttaaac tttgaaaact cggcctcatt ctggggttga    4200
actcccctcc ccaaatattg acacatggga agcagccaag tccttttgt tttttgtttg     4260
tgcggaggag tttccaggag tctttcccgg agccccttc cccacccaat gacgtcagtg     4320
gcattcactc ctcgctcctt gccttttctg attttttgtt aaaacttttc tccgcagcga    4380
gatgggggtt ggaggggtgg gagaaggagc tgattcaaag agccagtgcc ctgggggaa     4440
atagcaacaa gattacggct gcttctttcc gaggcaaagc ttaagaaggt gctaatccac    4500
tcggtcgcta attgagaggt tgtaaaaatg atactcgcct ccagttcgga cagaatcact    4560
tcccccccc ccgcccccc gcaagtccct cgctcatgca cagcggactt gagtcttgag      4620
tccaagcttc tttaatgctc gcttggaaag taaaaggaga gagaaagaga aagccgactt    4680
tcgctggtct gggactcagg gccgcggccc cacttgccgg catcctccga aagtcgcgct    4740
cctgcgaaat gaaacctcgc ccaggaggcc gcggacctgg acaccggcg ccacctcctt     4800
cacctctgac ccaggtttcc tcccggcgct gcgagctccc gggaagggt tagagccggc     4860
agccctcccc agcccgggga ggggagaggg ttatgcgacc ccacctctgg ctagggccgg    4920
ggaggccttt gcttcccggg agccctgccc gggctccttg gtcgcagggc tgctgggtcc    4980
caggcaggaa cgagagggtg aggcccacat gtggcccggc ggcccagggc ggcttgcagc    5040
gtcctcactg tccggctgc caggggctgc ggcgacgcgg ccagtcagca gcagttcag      5100
gtcgcgcaga ttttattgat gagctctgac tttcagcact ttccctaagt caagaagagt    5160
ctagcgtacc cttcggctgc ttcatttcag cctccctgcc tcagctcttc agccctattc    5220
cccctcgccc tgtcctgggg tgtgtacagc agcccaggcc ttccttctcc ttcccggctc    5280
cgtggcccga agccgccgag agagctcggg acagcgcagg accaggcagc cgctcgctct    5340
cctgtcacct taactgcagg ctccgagggg cgcctttgga gtgtactgag gtgtgtccta    5400
atcgtgcggc attcaacaaa tggacttctg gtgtgtggtc agaagagaaa agccatttac    5460
ttactttcct ccccggtttt ctggcaacag ctgaaggga gctgcctccg tggactgagc     5520
agacccagga gagggagtcg tggtgcggag acacacgcac cacacacaga tgaccggtgg    5580
cacacacgac acacgctgac ataccgacat cgccagtggg acacacacac acacacacac   5640
acacacacac acacacacag agagagagag agaatccctc ccagcattgg tcatccgccc    5700
ccccacccag gcttccactc cccctccct cttatctccc ctggcttccc ctcctctcgg     5760
gcgctgcgaa aagcagccgc acttagtcaa caaatggcac gtgggagaag ttggtgagtg    5820
tttggtgagg actcttcagg gcttttcaca agaaccctct gtacacaaag taagtggcgt    5880
gtttactcgg gcctctccag ccagagctgt gcctctgctc cgctgcgcac cgcggcttcc    5940
gaaaggagaa aggagagaag aaaggccggg gagagccggg tggaggattt ggacaggccc    6000
tggaggcttg ggctggggag gcctctggcc tcgtttagtt ctcggcccgg caacctcctc    6060
tcggcctagg cttcgccgcg gcctccgcag ctggaatgga gctgccagga cccagtgacg    6120
ctcccgcccc tttcctcttc ttccaagggg ccaggtgggc tggggtgcgg ccgccgctgt    6180
gctctgtgtc ttgggggcccc ggctgggatg gggtggggggc gggcggggc ggggcggcag   6240
gccacgctgt cctggagttg gcaagaaagg acagcacaga aacttgcacc ctccgaggac    6300
tgggagtccc gagtccagct tagggggagt gggggcgcga cccccaaccc agaaaccttc    6360
acttgaccgc tcaagttcgc ggcagcaggg cgggccgcgc cgaatctcgg cgtgcgcgga    6420
gcggggagat gcaggcgagc gccagagccc gggctcgggg gccctgcgcc ggggagagga    6480
```

```
gccgggaccc accggcggag ccgaaaacaa gtgtattcat attcaaacaa acggaccaat    6540
tgcaccaggc ggggagaggg agcatccaat cggctggcgc gaggcccgg cgctgctttg     6600
catasaagcaa tattttgtgt gagagcgagc ggtgcatttg catgttgcgg agtgattagt   6660
gggtttgaaa agggaaccgt ggctcggcct catttcccgc tctggttcag gcgcaggagg    6720
aagtgttttg ctggaggatg atgacagagg tcaggcttcg ctaatgggcc agtgaggagc    6780
ggtggaggcg aggccgggcg ccggcacaca cacattaaca cacttgagcc atcaccaatc    6840
agcataggtg tgctggctgc agccacttcc ctcacccaca ctctttatct ctcactctcc    6900
agccgctgac agcccatttt attgtcaatc tctgtctcct tcccaggaat ctgagaattg    6960
ctctcacaca ccaacccagc aacatccgtg gagaaaactc tcaccagcaa ctcctttaaa   7020
acaccgtcat ttcaaaccat tgtggtcttc aagcaacaac agcagcacaa aaaccccaa    7080
ccaaacaaaa ctcttgacag aagctgtgac aaccagaaag gatgcctcat aaaggtgagt    7140
ccgcttcttt cttctcgctt tattttttatt gcaatattca gacaggtctc cccccttcctc 7200
cccccttcct tcctcccctc tcgccggtcc cctcccccac tgctacgccg ggagagttgg   7260
gccggagaag tttccacgca ggagcccaaa cttttctactt ccagcgaaag cccgcgtcgg  7320
agggcgactg ccggcgagcg ggagcggcgc agggctcggg gcgggcggcc agctcagccc   7380
cagcgccagc gccagcgcca gcgcgggctg agctcgcggg aagaagggag actccaggcg   7440
cgacagcagc cgcggctcct agccccagcg tcgcccaatg ctcccgaccc gcgggaaaag   7500
acgaagaggc tctgtggtgc ccaaggccct ggaacggccg cagagagcaa ccgctgccgg   7560
ctgctttgtc cagcccgagg cccagcgaac gcgcagagag cgggcgctcc gaggactcgc   7620
cgagggagcg ccgagggaac ctgctcgccg cgtctccgcc cgcccgccgg ccctcgggct   7680
ttgtgccgca ctgggctccg gcgcagaaga gtcagccggc actcgagcgc cgaggggggc   7740
accgcgcccg ccaccagccc gagtggagtc agtcggcaag gcagccgcac gctggaggta   7800
gagggaagag cgagctagcg cgagccggga aggaagccac caggccaagg cggtggaacg   7860
cgcgctccga gggagctcag agccgagcgg gaggactgtc agcttccacc cagccccgg   7920
gctcttgccc ccaactccac tggagcgctg agctcggaac ttgaaaactc tctgctcccc   7980
aggcttcccc cgactctcat ctcccttgcc ttgcggaggc tggggctctt ccctgttctc    8040
cggcccctg cgcttggtgg gtattttttcc ttgttttcct ctgatccagt ctcaccaggt   8100
gttgggattt cagcaagttt tgaggtgcag agttggtttg cttttttgtt tgttttactc   8160
cgaatcccct tatgttttc ttggtaaggc cttgaaaata aatctgtatg aaagcattgg    8220
ccttcccct cgtctgatca cttcttctcc cggctaatta gtcggagtaa tttgagagct    8280
ttcgattcta agatcccagg aggaaaagtg tcttttcaaa gttcataaag ttgttgcctc   8340
tttccttgtg cagattttct cagtctccct gcgccataat agccctgaat tttagcaagt   8400
gtaattgggg gaaatggagt tgaatttcaa gtggaaatgc tttcttttttc gagtgctaaa   8460
acctggctct tcattcatga gcgatttcta gaaagtttaa aaacaaagtg aacgtggttt   8520
cttttctttct tcctttttat ttttcttata ctctcccaag ctccctaagc cattctggac   8580
gtttaactcg aacttgggaa ggttttagaa ggggctggga gcagaaaatg aaatgaaagg  8640
caaagagctt gagcctggcg agtttactga agagaaataa tagttgttgc ggttgacatt   8700
acatttttta tagccagtga cctttgcaaa agcgtgaagg cagttgatt agttgttatc    8760
ttatttggcc ctagagagta aaactttgtc atcataattg ctaattactc ttttggctgg   8820
gggcgggagg accgagagct ctccccttta cctcagttaa agagtttggg gatggaattt   8880
```

```
gagaattaag taattaaaaa aagaacagca tttgaaaact gaggcttgtg ttggggacag    8940
agaggtgggg gcagtgacca ctctcttgtg gtccaaggct ggggcgactc caaaatgtct    9000
ggagactcct tcgttcagga tgtggttcta tggccccagc gaggccgtac agagcctcgg    9060
gctgagctgg ggggctgagg ctgcagttgg gggtctgacc tctccggtgc acaggactgc    9120
ttccgggtgt cgatgtgccc cacttcccgg gttgcttctg cacttagtgt tcacgtttac    9180
ttaagtaatt agatagcttc ttagcgagag ggaagtggga atggagcaga actggaattt    9240
gaaatactac caccttccca gctgcttcga aaactaatca acgaggcctc tttgtgctca    9300
gctactgaat ttaaaaaaaa atggtatcaa gaagttacaa gccaggatgg gagcattctg    9360
ttgtgattgt gcacagcgtg ggttacaaag tggagttctg gaagttttac ccctcctagg    9420
ggaattccat tccccatctc cccacctact actcctttgc agcttcaggg tcctgcattt    9480
gttggggtgg ggtattttgc attagagttg gagattttgc ctatccaggg catggctatg    9540
ggtgccggga ctgagagaca ggaaggaagc attggagagc caacctagat aagggtaact    9600
agtaaccctc tgctgtggcc agtatttacc caatgctgag aaaaagtcct cattttcggt    9660
ttatttttat ggatttaagc tgtctaccaa gtagttaaaa agtagaccag gaatggcctt    9720
gtagagtaaa atgtgcttct tgaaattctt tgcttgcagg caggcagatc aataatcacc    9780
ataggtaaaa cagaaaaaat aatgcattta aaaaaaaaca gagagaaatg atgctgtgac    9840
tgttttgtta ttttacctct ttttgggggg cagacctctt gaatgggctc tttattgtaa    9900
ctctctcttc ccaattgagc tccccacggt gccgttgtat cttttacag cccctaacaa    9960 ctcacaccag taacacaatt acctccagat atttacaaca agaaattact tttctatttt    10020
ctccactcac ccaaaagact ttttttttt tcctttggg aaaggtaggg aggtgttcgt    10080
acgggagcag cctcggggac ccctgcactg ggtcagggct tatgaagcta gaagcgtccc    10140
tctgttccct ttgtgagttg gtgggttgtt ggtacatttg gttggaagct gtgttgctgg    10200
ttagggagac tcggttttgc tccttgggtt cgaggaaagc tggagaatag aagccattgt    10260
ttgccgtctg tcggctttgt cgaccacgct cacccctcc tgttcgtact ttttaaagca    10320
gtgaggcgag gtagacaggg tgtgtcacag tacagttaaa ggggtgaaga tctaaacgcc    10380
aaaagagaag ttaatcacaa taagtgaggt ttgggataaa aagttgggct tgccccttc    10440 aaagtcccag aaagctggga ggtagatgga gaggggccca ttgggaagtt ttttttggtgt    10500 agggagagga gtagaagata aagggtaagc agagtgttgg gttctggggg tcttgtgaag    10560
ttccttaagg aaggagggag tgtggccctg cagcccctccc aaactgctcc agcctatgct    10620
ctccggcacc aggaagttcc aaggttccct tcccctggtc tccaaacttc aggtattcct    10680
ctcccctcac accccttcaa cctcagctct tggcctctac tccttactcc actgttcctc    10740
ctgtttcccc cttcccctt tcctggttct ttatatttt gcaaagtggg atccgaactt    10800
gctagatttt ccaattctcc caagccagac cagagcagcc tcttttaaag gatgagact    10860 tctgtggcag atgccgctga aaatgtgggt gtaatgctgg gacttagagt ttgatgacag    10920
tttgactgag ccctagatgc atgtgttttt cctgagagtg aggctcagag agcccatgga    10980
cgtatgctgt tgaaccacag cttgatatac cttttttctcc ttctgttttg tcttaggggg    11040
aagactttaa ctaggggcgc gcagatgtgt gaggcctttt attgtgagag tggacagaca    11100
tccgagattt caggcaagtt ctgtggtggc tgctttgggc tcaaaaccca caaacagtca    11160
aaacaaacta tttcagtatg cttcttcact atagttcaga tagaagaaaa taaatcaaaa    11220
```

```
ttggggcatc gcttctactg attaaagggt taactgctaa agaatgtagg ggaaacagat    11280 tgggatatt  ccagtacttt gtttcaagcc ccaaagggta gattttgtat gcactgcagg    11340
gcagagctga gtgaccctca gatcgcccca agaggttgag tggatcaatt cctaaagaac    11400
ggagattctc ctgtcctagc cccaggtcca cctcggttgg gagttcaggc ctacctgatg    11460
cagctgcccg aggattaact cctatttcct tgctaacaga gccccatatt cgagcccgt     11520 ggaatcccgc ggcccccagc cagagccagc atgcagaaca gtaagtgcct ctggtctttc    11580
tgggacttcg ggctcggggt gcgcggaccc gagggtcagg ggaggacaca gggactcgcg    11640
acgcccgcgc tggcccggcc gccgaccgac tgaggcccgg ggacctgcgg cggctgctcc    11700
ccgctccgcg cccggcagcc cgggagggga gggcgtttgc ttggctcttc tcgatactgg    11760
agaagcaggg gctgggccct taagaacagc ccgcccgagt tttcgaagct gcggtagaga    11820
aaccccatcc ccccaaatc  ctgtaactca caccccctct cgccctgcc  cgggctctga    11880 ccccggagag aggggctggg ctgatcaggg cggggcgaag tcttctccta gttgagcgag    11940
aaggaggccc ctttgggctt agccaagact gaaagtctcc accaacccgg cggggttggg    12000
ggcttctctc cccaagtcac tctcagggca gctcctcccc tcctcacccc actacgggcc    12060
tagaagggat ggggagagga gccccccaggc ctgcagcagg gtaggggtgg taaactcgct    12120
gttacagggc gcgggagaga gcacggttta ctgggtctgg taaggaggtg cccaggaatt    12180
ggaaaatccc tgccctggca actgcaattg cttgggtcct gatagtccca ggcccagagc    12240
gcttttgata cttatggccc ttgtacctcc ctgctttcct ctgcccagac ccgtggggt     12300 cccacccacc ttcctgttcg tggtgggtgc tggtacgcgg cagggctagt ctagagctcc    12360
gacctgggag cctggaggcc cagcgaaacc aggcccggtt tgaggttacg gttgaggcac    12420
acggcgtcgg ggctcaactg aactcaaagt gtggaaaggc ccgggtcttc cagcagcctg    12480
ccctggccga accacacagg cttaaggagg gtccccagca ccttatccat ctgttttgga    12540
aacgccggtc gcccctggt  gcttccgggg ctggtaagcg cgtagctgag gaaagggcac    12600
aaaggtggcg agctttgcgg gagtagttgt gcagaacctg ccggacccca gggcttggcc    12660
ggtaggctcg ccttcggcgg ctgggctctc cccttggagc tcagactccc cagccgcagg    12720
ctgtctctcg ggcgggcccc agccagggcg cgcagccctg agcgtttgtc gctgcggccc    12780
ggctggcagg ccccgagggg cgcggggtcg cgggccggcc ggcagggctt tgtgccgctc    12840
gttcccgggt gtgcgcgagg cgcggagcat ccaaattgac accatatgtt ttcctattag    12900
ttgcttcgcg gtcgagttct aggcgcataa tcatcgccag tgggcgagag cgccagcagt    12960
ccctagggaa gggacacaat gattgaggct taacctctga aggggaattt ggagctgcgc    13020
tttctctctg ccatttcgat gctgggagtg gcgctctggc cctggcgtct cctgggcaag    13080
caccagccgg cggtatctgc ggaggtggct ggcacgttgt tattttttga aatgagtgag    13140
gagggaggtc tagatttagg cggccttacg cgcccgcctt ggcattagca gactgggaat    13200
tgccgtggct atgcccgaag tttggaaagt ctctctcggt ctctttctgg acagcctttt    13260
ctttttccgg gaagcttcct gtgcctagag gtggggctct gtagctggag gggtagatgg    13320
aacttgcgaa gcaaaggaag gcaataaaag gaagttagga gaaaccggaa acgtgggcca    13380
ggccttgctc tgttggagaa gcggtgtccc cgcaaagtcc ctgcttgcgc tggtcccggc    13440
cggagcccag atcccccaaa cgcctgtcac ttctcatcga gttgaggctc cggcccccac    13500
ccgcgccttg gtgagggccc cccctcagcc ccaagccttc ggctaccctg aaaacgcggc    13560
tcccctcgaa ggggaaacaa gtgcagttca atctcgtctg agtgatctac aaataaggac    13620
```

```
ggaaagggtc gttttatcac ggtcccgttt gtcgtgacga tgcaatttcc cggagcggag   13680
cactgtcaca aagtgacaag gctgccacaa gcgccccgac tgatcttttc aattagcctt   13740
ccatgcatga tccggagcga cttccgccta tttccagaaa ttaagctcaa acttgacgtg   13800
cagctagttt tattttaaag acaaatgtca gagaggctca tcatattttc ccccctcttc   13860
tatatttgga gcttatttat tgctaagaag ctcaggctcc tggcgtcaat ttatcagtag   13920
gctccaagga gaagagagga gaggagagga gagctgaaca gggagccacg tcttttcctg   13980
ggagggctgc tatctaagtc ggggctgcag gttggagatt tttaaggaag tggaaattgg   14040
caattggctt tgtgtgtctg tggttttttgg ggagggggac tacaaagagg gctaactcc   14100 ctctccctat tctctaaggt tggaccacag ggatgaggtt gtgagataca aagataaagg   14160
agggatgggg aacactatga tgtggtattt ttcttttctg tttttctttt ttgataatat   14220
ctatccttgg ctaaggggag ggcggagttc agcggcggaa ataaagcgag cagtggctgg   14280
tgcgaaccga ctcccggctc taagccttac ttgcggtggc cggacttgtc tgtggctgaa   14340
gccgagcccg ggctctgact ctcacgtctg cactggaggt gcggaaacct ggactggggt   14400
tcaccagcca catactggct gctctggttg ttctctcctc ttccttcttc tattctaacc   14460
aaacaaaacc caactcgatg cttgtgccag gccttggcca gtttggacgg tgatggaaac   14520
atttctggat tttagcgtct aagggagcac tcaagggctg taaggtttgc tatcactgtc   14580
ccaacactgc agagaccttg aaggttcagt gtgggatctg tagaacccat ggtttgcggt   14640
gacactcaga ggggatcttt gggagattta tagagccggt tcttagcgct ttgtgggttc   14700
agaggctggc tgcagtgttt atgaagaggg gcagtgggct ggggacactg ctggggttat   14760
ggctgtagtg aggtccatgt gtacttgttc cttggcatgt gtctgactct gtgttgctgc   14820
tgcagtacag tgggcagggg cacggttgct tggactgggc tgcccgatgt ctggcatggc   14880
tggtggtcct gttgtccttt atttgatcga tagcagggaa ctgaccgccg aggttggcac   14940
aggttggcag ggggatgagg atgcattgtg gttgtctcct cctcctctcc ttcttcctct   15000
tccccttcct cctctccttt ctgttcttgt tctccctcat cttcctcttc cttcttctcc   15060
ctcttcttcc tcttcactct gctctcttct cttcttttcc cctttcctct cctctcccct   15120
tcctcaggtc acagcggagt gaatcagctc ggtggtgtct ttgtcaacgg cggccactg    15180 ccggactcca cccggcagaa gattgtagag ctagctcaca gcggggcccg gccgtgcgac   15240
atttcccgaa ttctgcaggt gatcctcccg gcgccgcccc actcgccgcc cccgcggccc   15300
tccactctca acgccctctc ttcatttctt actgtaaacg atgctaatta tggaccccc    15360 caccctcacc caccccagtc cccagtcccc ccacccactc ccctgccttc ccactttccc   15420
ctctccttcc accatccttc cctatctctt tcaacctggg tcagttacat aagataactc   15480
atctgcttca gaaaaatatt gtgtgcggat tttttttaaaa aaatctttct cttttttattt 15540 ggtaaagaca ttcattgtgg aacagttta tgaaccgtaa taagctgagt tatataaacc    15600
ggcataattt cattctgctc tccccagccc atgcttacct cagcttttga ggtatttgtt   15660
tattcttcat gttatgaat aatatatatt gattttaaaa ggcaaatgct atttactcct    15720
ccctaactca catttactca attgagtatt ttttaaagaa gaagagtaa aaaaatcagt    15780 ttatttttta cctttgttct ttaaaacata acgccacttt aagcaaggtc agcacaaaaa   15840
taaatttatc tacttcgttt tgatgcatct tcaggcagtg tttaagaaaa gttttttttt   15900
taaaaaaagc ttttaaattc gttttttagt tcaaattgtt tgaaagtatc atcatatttg   15960
```

```
tagtttttag ggctacaaat gtaattttaa gaaaaaaagc tctctacagt aagttctcat   16020
accattgaag gtatatttt  gtgttataga cccatgcaga tgcaaaagtc caagtgctgg   16080
acaatcaaaa cgtaagcttg tcattgttta atgcatactt aaacaatttt attttgtct   16140 tgaaattatt aataatgtgg ttttctgtcc acttccccta tgcaggtgtc caacggatgt   16200
gtgagtaaaa ttctgggcag gtattacgag actggctcca tcagacccag ggcaatcggt   16260
ggtagtaaac cgagagtagc gactccagaa gttgtaagca aaatagccca gtataagcgg   16320
gagtgcccgt ccatctttgc ttgggaaatc cgagacagat tactgtccga gggggtctgt   16380
accaacgata acataccaag cgtaagttca ttgagaacat ctgccctccc tgccctaagc   16440
ccaatgctct ctcctcttta cctcctccca ccctctctct ccactgtctc ttagtctgtg   16500
tcctctccct gctccacatt tgtctccttt gtacctgggg gaacagagag gaatgccctg   16560
acttttcttt gactgtctgg aaaatgggag tcaagtgtgg ggagtcattc acttcatttg   16620
catgctgcaa aacagagggc ggaggcacca gggaaaggca cttgaatgaa gaaggaaaat   16680
gagaaccaga ttgtaacttc gtcctaatcc acctgccaga actttccttc aggtgtcaca   16740
catccatttc catcctaata ttaaacaata taatgaaaga aagctttaca acaagtctaa   16800
atagttttta ttttcgggca gtcttttaac aaagcaaagc aaccgtgtga gttaggtcac   16860
cagagacacc aagcaatggt gaaggacccc ctccgcccaa ttctctatcc aactaaattt   16920
ccatgcccaa agtgatagct atcattttt  ccacggtgta tctgcaaatc cacccactgt   16980
cccggggtgg ctgggagctt tttaacgggt tgagagttgc ttttaaggt  tgtgggtgag   17040 ctgagatggg tgactgtgtc ttcaggagac actaccattt ggtttgattt tggtttgatt   17100
tgcaggtgtc atcaataaac agagttcttc gcaacctggc tagcgaaaag caacagatgg   17160
gcgcagacgg catgtatgat aaactaagga tgttgaacgg gcagaccgga agctggggca   17220
cccgccctgg ttggtatccg gggacttcgg tgccagggca acctacgcaa ggtaaaaccc   17280
aagcagccat ccacgcagct ctccatatgt gcatcccttt gcctgtcccc tactctccca   17340
accatttcct ctcagggctt ccatgcttgg ggaatgtcat gggtgagact gcatttgaag   17400
gcctgggaca catcgaccac attgtatgta ggtggtgttt gttgaaccat tttgttggcc   17460
tgggaatgtg agggttgtgt atgtcaggag cggtatgaag gtggctggtg ggtgcgtgtg   17520
tgtgtttgtg ggcagcactg tgtgcataag aacgagctgc gtggtgcact attcaaatt    17580 gacattagaa tgcagggaga gccccttgt  agaagtgtga caagataacg cactgacaga   17640
ctgcgaggtt aacataattg tatcctgttg ctttttgctg taattgacaa attatgtgac   17700
tatgagtagg gtgcacatga aaaggtgagc agggagatgc agggcgagtc ggggatgggg   17760
cattggaagt ggtggtctcc caactaaaac caccccacta tccttgcccc tccccgttc    17820 gcccctctgg gtcccacttt ctcactctct gtgggtggcg actatgtgga agtggtgagg   17880
tgaagatact gtgagcagga cggcgggatg ccggggagccg ctctggtctg ggaggagaga   17940
tgggacctga aacaccccag gttctgtgag aagggctgga ggaagaagag cggggatgg    18000 gggggtggg  gcggagggga gggtcagttg gctcccctcc gctcccctcc acccccgag    18060 gtagcttggt caagaatagg aaacagttta ctccgaagat taatcggtat ttgttgtcct   18120
cgtgacaagg agataatatg cgggataatg ggacgtggcg tctcactccc aggagcacaa   18180
cggagccgag gggctcgggg ccaggggcgg cgcgcgggac tgcgaggagg ctgccggcgc   18240
atccgtgagc tctcggaccg gctccggatg cccggcgcct ccatggagtc gggcgaggga   18300
agggaaaatc ggtaacagta tgcgaaatat ctggtacaaa ggatgcttct gtcactcgca   18360
```

```
agaatttgtt atgggaacaa tcctgtcgct ctgtaattgc tcattagaga acgttttgtt    18420
tctcattaag gcgacatgaa taagcgtcta gttgaaggag acagctgtag aaatgttcca    18480
caagagacct ctggacacga ttcggcacca attgccaatt agacatgtca gttttaagag    18540
cagaaaacaa tataggacgg acactgggaa gatagggagc aaagcgctcg cttcttgttt    18600
cccagcgcgg ccgctcggcc ggcggaggcc tcctgacgcg cggggcccgg gctccctgg     18660 gcgacccgc ccgcacgggc cccgaacccg ccgcctccgc gagctcagag ggccccagg      18720 cccgctcccg cctctggtga gactagcgat tgaccccacc gagtgtaggc aaccccatcc    18780
ctgcctgact tttgaaaccg taggattccc acttgtagac actggacaca cccaagtgac    18840
acccgaactt cgcactcacg agcgtccacc cctccgcccc cagcaatctg aggtcctggt    18900
gatccctccc ctgacaagag tctggcccac ttagtccgag aagtcttggg gagggactca    18960
gggcacggtg gcctaggcct gggagggctg agcccagagc ctccactccg ggctctcccc    19020
ggtgcgtggg ctcccatgag cttggggcgc aggatacacc cccttccgc ttcttggagt     19080 tgggcagaag ccgaggacag cagcttccac cagaggtggc gcccgattcg ggcggatttt    19140
cgtcgccgga agtctgaggg cgggaagtga gagtcaaatc agctagggtc cgcctgtgat    19200
ggttggggcc ggaggtggag ctagtccagg ggcttttcac tttaacgcgc ctagttgcta    19260
gaaaattctg ggtcaactgg caatcaccac ccccccaccc gcaagtgagg ttttggggg     19320 gtgattgtca cctcaggcac aggaccgtcg cccctagttg cgtggggagg acacgtgggc    19380
caaacgaagc acagagttgc cggcgtgggg gtagcgggca ccgtggtga gcttcgcttc     19440 acgttcccgg ggaatcctca gacttttgg tgctaagagg gtccccctcc ctccctagcc     19500 cccttttccca gcccaggaag cctttcttgg gttttaaaga gtccatactc caaaagcata   19560
aggcgggggt taggtctcag agggagacaa atatggtttc catctgatca acgccatgcg    19620
gcggtgaata aaatcgcgac gacgtgggct gacaacaaca agagacaact ctatccagcc    19680
ccaattctcc ggcgatttgg tggttttagg gatcacggag acactttttc ttatctcctc    19740
ccctcacccc accccaccc cccataatac ccaagccctc tataggattt agtcagcctc     19800
tctttcaaca gatgctacaa tgttttgatc cgcgctccag agctgaaaag gtgccgcaac    19860
cgggttgcta tctttcttg cttgtttttcc gcctcactga ttaagacact aagaaactaa    19920
ggaatgattt tatttcccag caactctctc tctgtctctc tctctctctc tctctctcac    19980
ctccttccag gaaacaaatc ctattccat cgtcagatgg tcctggggct gggataatgg      20040
gaggcgcttt cactcgcttt ctcacggatt aggctggaag gtgaacggca cccactgaag    20100
gcccctgctt tgcgcggctc cgaggggcg cctttgaag aagatatctt aattgtccac       20160
cacttaggtt tatcgtgggg gtggggagt cgagatccaa cttctagttt tattttgtta     20220
aaagctttaa gagtggaagg caaatccact aaagtggggg gaaatgtacc cattttatgt    20280
aagagcagcc gctaggtcac cgcctggctg caaacagttg ccacttctaa agtaatgaac    20340
tgtctccgtg ccgctctccc cgcggggtag agaagggatc ctgcagcgac aggtttcttt    20400
ttgctgtgga attccaatcc ccgcttccca tcttttttt ttttttttt ttttccagat      20460 ttaaaattga gctctactgt ccctgctgac ttttctctct taagtgtcag ttctggagcc    20520
agcacagggc ctggcggcga tcgcgtgctg cctgtgtaaa cccgtgtgta tgtttgtgtg    20580
agacagaaca tggataagaa tgtgaatctc catgttttaa aattaagaaa atgtcaaaga    20640
ggcaaatgag agcagagcat gctatcggcg gggttcttcg gaggcagatt cgggcaactt    20700
```

```
tgtttaattg gcgagatcga atgtgccaga aaagggaccg agatggggcc cctaggaagg    20760
catgggcatg agtggccatg gggagatggg cattgtgttc tcctcagtgt cccccacccc    20820
ataccagatg tgcacagatt tttgtctgtt ttccaaaagc aataaccctc cggcctttct    20880
agttggccaa aaggagctat ttccagtctt ccttcttcac caaacccgaa aataaagcga    20940
ggggtggggg tggtcgcttc atttcttccc ttgaaaaacg ctttgaaaag tccccggaaa    21000 cttgggcag  taaattagca cagacgcttg tgcccgcaca cgtgagcgga gcgcgtctcc    21060
ctcagctaag tagccctcct cgaccccac  ctttctgatg gagtgcaaag acccagagtc    21120
cagatggggc tcagttacta atattctctg gccctcatcc tccttttcct ctctctccca    21180
ctcttgttcg gccctcgtgt ctctttttcc tctcagcatt cttttctgtc cttttttaaa    21240
aatacctttc tagcctctat gttttttgag ccttcttttc ccctccatcg ccctcttttt    21300
ccctccatcg ccctctgtct ttcccctaac ccaggccccc caatccttcc cccttgcttc    21360
cacccccacc gctggtttcc atcctgcctc cctccatct  cctctatgta ggaacccagc    21420
cctggtcccc gtccactctc cctgcctccc ccatgctgg  gccctggccc cccatccac    21480 cctccatccc cccagccaag cgccctaaat agcacggagg cgcccgctct tcggacagtg    21540
attaatgata gcagagcaga ggggttaaca cacttcactg aaaagtctgt tgactgggct    21600
tcttgtaaca caatgtggcc cgctgcacgc ctcaagagaa tccttttgtt gtccgcgctc    21660
attgtagcct caaaattctg cccacgaaag tttgccaacg ctcctgcccc aggagtttaa    21720
tagtttccct tactcgcggg gcattgtgca gcgctgaaaa gcagcccctc gctattcaag    21780
tgttggtggt catctcaata gatctccaag ggcccatatg gtggccagtg ccgatgaatc    21840
cgcctgttta aatggggag  aaagttgggg ttttaaaaca tttcaaagtt cctgaaaaga    21900
tcccactaga tcctgtcaca attccctgaa ctctttgaag gcgcagccta ttgtctcctg    21960
gttataaata atattcctgg ccaagtcgat tcccaccaag gcgctcctag ggccccctcc    22020
accccgcctc tggccaagtt ttgaggatag ggaggtgggt agcccatgct ggtatccctt    22080
gggggtcatt tcaggacccc agacccagga cccagcctgt agtggccctg gaggcccagt    22140
cagagtttag gcaatcctgc ttcccttcac tgtggcctta caggcaaggt gcaagccggg    22200
agccagctag cccaagtgca catcttgccc tccaggcagc aagggaaaac cataaaactt    22260
tccccctgta taatgataga agttacattc aaagtggtgg aaatgcccta attaaaaatg    22320
taccacttaa atgatatgcc aaagattcag ctgcagcata gaatatttag ctagttagtg    22380
aactctctac tatttctttt ttaaaattac acgttaaaaa tttaaaagaa atcttacttt    22440
tctctggtgc aacacattac aaagaatgga cagtcctttt atctaaatat aaaattccat    22500
tttcagcaat tatagcctgt tcttggtgat gatataatta cagctgtgct cgtaataggt    22560
gtcaaggcga agcgcactca tacaatagtt gaataaaact gcagaacaat gcgagcactt    22620
ctaaattcac aacctttaaa tgaaattgac tgtgcagaat tcaaataaaa actagataaa    22680 tatttttttaa aaaagattac aagcttggtt tggtttctta atagcatttt ctacaaacct    22740
atcaacatct aattgattag ataggaatta ctgattatag atcaactgaa atcttgaaca    22800
tcactcttct attttcccaa cacagccata ggtaaagaga ttctgtaggg agtggagtga    22860
ggcatttggg gagttggggt tacttataaa agatcatttt aattggaaac ttcagtgctt    22920
attttttcat tcaagaaatg ccacttagtg tgtgtattat aaagtctcat cttgataaaa    22980
acaaagaaaa tggtggtcag gtaactaaca tcgcaaatgt attttttaa  aagaaggctg    23040 acagttacct tgggaatgtt ttggtgaggc tgtcgggata taatgctctt ggagtttaag    23100
```

```
actacaccag gcccctttg gaggctccaa gttaatccaa atttctctta ccatcctatt    23160 cttttgttc cagatggctg ccagcaacag gaaggagggg gagagaatac caactccatc    23220
agttccaacg gagaagattc agatgaggct caaatgcgac ttcagctgaa gcggaagctg    23280
caaagaaata gaacatcctt tacccaagag caaattgagg ccctggagaa aggtgataga    23340
gtttttcaaa gtagagaagc agtaaatcaa agtaaatgcc acatcttcag tacaaagagc    23400
taaatttagc cagggccctt tgcatagaag aatgaaaaga tttccttttt tctgtctttt    23460
tatttctctg ggcatctttt cagtgtgtgt gtgtgtgtgt gtgtgtgtgt gtgtgtgtgt    23520
gtgtgtgtgt gtgtgtgtgt ggtgtgtgtg tgtgtgtttc ttcttttcat ctaccagtaa    23580
ttcaaagact aaatgtctga cttataagga aaaatgatga tttggctatt tcaggccaca    23640
gaaaggtcac tgaatgccat tccaaagaaa atttaacttg gttctggtgg aaagttctt    23700 ccaagtacag tcaacactag aagcatttta aagggaattg gttggaggta atgggagtgg    23760
ggaggtggga accagtttga tgcacagttt ggtcaacata ttttgtgtag ttctggcaca    23820
atatggaaaa tcaacttact cttcagagt ttgagagaac ccattatcca gatgtgtttg    23880
cccgagaaag actagcagcc aaaatagatc tacctgaagc aagaatacag gtaccgagag    23940
actgtgcagt ttcacacttt gtgattcata ccatttgtct ttcctagaga cagaggtgct    24000
tgtacagagt actatttatt tataggacta atataataaa aaggttcagt ctgctaaatg    24060
ctctgctgcc atgggcgtgg ggagggcagc agtggaggtg ccaaggtggg gctgggctcg    24120
acgtagacac agtgctaacc tgtcccacct gatttccagg tatggttttc taatcgaagg    24180
gccaaatgga gaagagaaga aaaactgagg aatcagagaa gacaggccag caacacacct    24240
agtcatattc ctatcagcag tagtttcagc accagtgtct accaaccaat tccacaaccc    24300
accacaccgg gtaatttgaa atactaatac tacgaatcaa tgtctttaaa cctgtttgct    24360
ccgggctctg actctcactc tgactactgt catttctctt gccctcagtt tcctccttca    24420
catctggctc catgttgggc cgaacagaca cagccctcac aaacacctac agcgctctgc    24480
cgcctatgcc cagcttcacc atggcaaata acctgcctat gcaagtaagt gcggctggtg    24540
gtggcctgca taacccaggc cccagagaag tgaggagtgg ctcagggcct gcggacctca    24600
ttggctgtgt ctgcacccett gagagctttt cgcactacag tgattggctt gaccagtcaa    24660
gtcggagaca gtcaatccca tcactttaa gtgattgact cattaattca tgccctaaaa    24720
aaatgagtaa taaaaatctg tccagttttg tcaggttgat ctgccttta ttatactgtt    24780 accttgataa tgttgggtgg tggtgggca tgttgggt accagggagc cttgcaccag    24840
aaagtggaaa taatgctggc acattatcag atagcagatt agtagtttaa aatttgggtt    24900
tatattaatg tgtttgtatg ctaaatatag aatctgtgca cgcatttggg gcattacttt    24960
gggtatatgt gataaactag tgagaaagaa aaaggatca gaaatgggat tcatatttac    25020
atggtgagat atacataata taatgagaat gctagttttc tgtctgtatc tacaataaga    25080
aaaggcatag caggtatttg ctggaaattt agtgtgtctt tgctgtgaat ggtgtgacga    25140
gtttgtggcc ctcctagctg cctgggaagc ttgatgctat tcacttggta tgacagcctg    25200
cctctcctct tagttctgtc ccaaatatct attagcccct acatttagag gtcctgcact    25260
aggttcaccc tttatgatgt aagttggata aggcagatgg tttgtactag acctttgttg    25320
ctggatggat tcttgatagg aaaaatgtct gtccttctggt aggcctttcc cagtggtttt    25380
cctagaactc ctgtttgtgc aacaattaga gatattagat ggtacgatat tggccagcat    25440
```

```
gagcctctgc tggaaacagt tctggggcta cactgattgt ttattctcca ttgaacattt    25500
tttgctggat ttcaaatcca aataacagca aaataaatgt ttcacagtct tcagactaat    25560
ataggagcag ctagataagc aacttcagag gaattattca catgtttatt tttattgcat    25620
ctggatattg ttggccatag tgcaattgat gtaaattaag ggattaacag cccattagtt    25680
ggtgttgcta taactgcgtt ggaattttcc agaagtcagg ttgcctagag gaactcattg    25740
caggaattag aaacaaatgc aagctgaaat tctggcaggc cctcaaggcc tgtttgcctc    25800
tttgaacttg atgttagcat tcatcatctg actttaataa ggccacagag tgtctcgttc    25860
agtttcatgt attataacaa catccaggtt tctgtgaaga tagcaaaatg tgtatgtgag    25920
aaaataataa gacgaacaag tagatgctgc aattatatta gggctgtttc cacatacaga    25980
gcggtatggg gaatcaatct atttcaaaca ctgactttta aaaattacat aatttgtata    26040
attcaaaaag tacatgcatt cattaagcat aaagaaaatc aaaatgatca ataactttac    26100
tcttcagaga aaactactct ttgaattttg gagtgggtga gcccgattgt ctatccattt    26160
attcattctc ttgaccaaaa tcatcatttt acaaatggtg ggtgtcttcc tctggacctt    26220
ctctgatatg cttccctctc tgagcatatg gattttggaa attaaacatt tctccagttt    26280
gcagagaaga gaaatgatag tatactgtac tatcatctga cctgcttgtt cccgacacac    26340 ttctttta at tcatcccaag tttgctgcca tggcatagta ccatgagagc tcatgaggcg    26400
ttttgttagg agaaaggttt acctcctcag tgctgccatt ccgaacagtt cgagggtagc    26460
aacagttttc tagttataag tcagtctggg cttttgggtc tgttaggaag tcatggttaa    26520
ttctcaggat ggaggtcgtt atatttacta acacttctga tcactttaac ttggggtcat    26580
tacagatctg cttcttcaaa gaatctttaa tcccatcagt gaaaggttcc caaggtccct    26640
gaaccatact ttactgagag ctcctcccac tgctctctgt cccaaagctt gagatatggg    26700 ctctggggt catagggttc ccaaataaat ccagatttgc agggagaggg gatgtgtttt    26760
gatgaaggtc ctcatgctat aggttcttca aagatgctag cagaggttag agacaaaaat    26820
cctattaatt tatggatagt ggcaaccatc tagctggaca gttgtcagaa cctaaagtgc    26880
tttagaggct tgatacatag gcagcttttct tctagctgtg gccagtggaa ggactagctc    26940
gaggcccaat cttagattta tcatatggaa ttccagtact tcacgtgaag gcatctttaa    27000
tgatcagact tgttggcaga gttcctcggg aggagggagc ctggggctgt ggctgtgtga    27060
tgtgttcctc agtaaccaca ggtttgcctc tctcctcaca gcccccagtc cccagccaga    27120
cctcctcata ctcctgcatg ctgcccacca gcccttcggt gaatgggcgg agttatgata    27180
cctacacccc cccacatatg cagacacaca tgaacagtca gccaatgggc acctcgggca    27240
ccacttcaac aggtgagcca ctgctttctg caggctgcac agaggcgatc tctcttcact    27300
agaagtttac ccaaacagaa tctcctggtc ttatgggagg gcgtgtttaa ctccttgctt    27360
tccttgtccc tgggggatgg ggattgaaaa gggaaattca gttaagctaa ttagtaactt    27420
tacaccatat agacaaaaac taaaattgtt tttcctgaat ttggtcacaa aagttgtgta    27480
tgaagacaag gcctgagact gcaagttttc tgaggacaga ttattagacg aagctcagta    27540
gggggcccac tgagctgtag gtgcgtgctt gttgaaatgc ttcttgccct catagctcct    27600
ctagaccttt tgctggaaat aaaaagtgac acattggttt tccagagaca gctttattgt    27660
aaaagttcca aacatgcaaa caaacagagg attttttttt tcttttcctt tggattgggg    27720 tgggggtac ttgggatcca ataggtatat atacatatat tgtctagttt ctgaaggtgc    27780 tactttatt tgtaacaatt gaagtgattt taatacagta aaaaatgtta gaaagtatta    27840
```

```
gtttttttttt ttttttttttt ttttgtaaac ctataaattt gtattccatg tctgtttctc   27900
aaagggaata tctacatggc tatttctttc atccacttct aggactcatt tcccctggtg   27960
tgtcagttcc agttcaagtt cccggaagtg aacctgatat gtctcaatac tggccaagat   28020
tacagtaaaa aaaaaaaaaa aaaaaaaag gaaaggaaat attgtgttaa ttcagtcagt   28080
gactatgggg acacaacagt tgagctttca ggaagaaag aaaaatggct gttagagccg   28140
cttcagttct acaattgtgt cctgtattgt accactgggg aaggaatgga cttgaaacaa   28200
ggacctttgt atacagaagg cacgatatca gttggaacaa atcttcattt tggtatccaa   28260
acttttattc attttggtgt attatttgta aatgggcatt tgtatgttat aatgaaaaaa   28320
agaacaatgt agactggatg gatgtttgat ctgtgttggt catgaagttg ttttttttt   28380 ttttaaaaag aaaaccatga tcaacaagct ttgccacgaa tttaagagtt ttatcaagat   28440
atatcgaata cttctaccca tctgttcata gtttatggac tgatgttcca agtttgtatc   28500
attcctttgc atataattaa acctggaaca acatgcacta gatttatgtc agaaatatct   28560
gttggttttc caaggttgt taacagatga agtttatgtg caaaaaggg taagatataa   28620 attcaaggaa gaaaaaaagt tgatagctaa aaggtagagt gtgtcttcga tataatccaa   28680
tttgttttat gtcaaaatgt aagtatttgt cttccctaga aatcctcaga atgatttcta   28740
taataaagtt aatttcattt atatttgaca agaatataga tgttttatac acattttcat   28800
gcaatcatac gtttcttttt tggccagcaa aagttaattg ttcttagata tagttgtatt   28860
actgttcacg gtccaatcat tttgtgcatc tagagttcat tcctaatcaa ttaaaagtgc   28920
ttgcaagagt tttaaactta agtgttttga agttgttcac aactacatat caaaattaac   28980
cattgttgat tgtaaaaaac catgccaaag cctttgtatt tccttttatta tacagttttc   29040 tttttaacct tatagtgtgg tgttacaaat tttatttcca tgttagatca acattctaaa   29100
ccaatggtta cttcacaca cactctgttt tacatcctga tgatccttaa aaaataatcc   29160
ttatagatac cataaatcaa aaacgtgtta gaaaaaaatt ccacttacag cagggtgtag   29220
atctgtgccc atttataccc acaacatata tacaaaatgg taacatttcc cagttagcca   29280
tttaattcta aagctcaaag tctagaaata atttaaaaat gcaacaagcg attagctagg   29340
aattgttttt tgaattagga ctggcatttt caatctgggc agatttccat tgtcagccta   29400
tttcaacaat gatttcactg aagtatattc aaaagtagat ttcttaaagg actttctg   29460 aaagctgttg ccttttttcaa ataggccctc tccctttttct gtctccctcc cctttgcaca   29520
agaggcatca tttcccattg aaccactaca gctgttccca tttgaatctt gctttctgtg   29580
cggttgtgga tggttggagg gtggagggg gatgttgcat gtcaaggaat aatgagcaca   29640
gacacatcaa cagacaacaa caaagcagac tgtgactggc cggtgggaat taaaggcctt   29700
cagtcattgg cagcttaagc caaacattcc caaatctatg aagcagggcc cattgttggt   29760
cagttgttat ttgcaatgaa gcacagttct gatcatgttt aaagtggagg cacgcagggc   29820
aggagtgctt gagcccaagc aaaggatgga aaaaaataag cctttgttgg gtaaaaaagg   29880
actgtctgag actttcattt gttctgtgca acatataagt caatacagat aagtcttcct   29940
ctgcaaactt cactaaaaag cctggggggtt ctggcagtct agattaaaat gcttgcacat   30000
gcagaaacct ctggggacaa agacacactt ccactgaatt atactctgct ttaaaaaaat   30060
ccccaaaagc aaatgatcag aaatgtagaa attaatggaa ggatttaaac atgaccttct   30120
cgttcaatat ctactgtttt ttagttaagg aattacttgt gaacagataa ttgagattca   30180
```

```
ttgctccggc atgaaatata ctaataattt tattccacca gagttgctgc acatttggag   30240
acaccttcct aagttgcagt ttttgtatgt gtgcatgtag ttttgttcag tgtcagcctg   30300
cactgcacag cagcacattt ctgcagggga gtgagcacac atacgcactg ttggtacaat   30360
tgccggtgca gacatttcta cctcctgaca ttttgcagcc tacattccct gagggctgtg   30420
tgctgaggga actgtcagag aagggctatg tgggagtgca tgccacagct gctggctggc   30480
ttacttcttc cttctcgctg gctgtaattt ccaccacggt caggcagcca gttccggccc   30540
acggttctgt tgtgtagaca gcagagactt tggagacccg gatgtcgcac gccaggtgca   30600
agaggtggga atgggagaaa aggagtgacg tgggagcgga gggtctgtat gtgtgcactt   30660
gggcacgtat atgtgtgctc tgaaggtcag gattgccagg gcaaagtagc acagtctggt   30720
atagtctgaa gaagcggctg ctcagctgca gaagccctct ggtccggcag gatgggaacg   30780
gctgccttgc cttctgccca caccctaggg acatgagctg tccttccaaa cagagctcca   30840
ggcactctct tggggacagc atggcaggct ctgtgtggta gcagtgcctg ggagttggcc   30900
ttttactcat tgttgaaata attttgtttt attatttatt taacgataca tatatttata   30960
tatttatcaa tggggtatct gcagggatgt tttgacacca tcttccagga tggagattat   31020
ttgtgaagac ttcagtagaa tcccaggact aaacgtctaa attttttctc caaacttgac   31080
tgacttggga aaaccaggtg aatagaataa gagctgaatg ttttaagtaa taaacgttca   31140
aactgctcta agtaaaaaaa tgcattttac tgcaatgaat ttctagaata tttttccccc   31200
aaagctatgc ctcctaaccc ttaaatggtg aacaactggt ttcttgctac agctcactgc   31260
catttcttct tactatcatc actaggtttc ctaagattca ctcatacagt attatttgaa   31320
gattcagctt tgttctgtga atgtcatctt aggattgtgt ctatattctt ttgcttattt   31380 cttttttactc tgggcctctc atactagtaa gattttaaaa agccttttct tctctgtatg   31440
tttggctcac caaggcgaaa tatatattct tctcttttc atttctcaag aataaacctc   31500
atctgctttt ttgtttttct gtgtttggc ttggtactga atgactcaac tgctcggttt   31560
taaagttcaa agtgtaagta cttagggtta gtactgctta tttcaataat gttgacggtg   31620
actatctttg gaaagcagta acatgctgtc ttagaaatga cattaataat gggcttaaac   31680
aaatgaatag gggggtcccc ccactctcct tttgtatgcc tatgtgtgtc tgatttgtta   31740
aaagatggac agggaattga ttgcagagtg tcgcttcctt ctaaagtagt tttattttgt   31800
ctactgttag tatttaaaga tcctggaggt ggacataagg aataaatgga agagaaaagt   31860
agatattgta tggtggctac taaaaggaaa ttcaaaaagt cttagaaccc gagcacctga   31920
gcaaactgca gtagtcaaaa tatttatctc atgttaaaga aaggcaaatc tagtgtaaga   31980
aatgagtacc atatagggtt ttgaagttca tatactagaa acacttaaaa gatatcattt   32040
cagatattac gtttggcatt gttcttaagt atttatatct ttgagtcaag ctgataatta   32100
aaaaaaatct gttaatggag tgtatatttc ataatgtatc aaaatggtgt ctatacctaa   32160
ggtagcatta ttgaagagag atatgtttat gtagtaagtt attaacataa tgagtaacaa   32220
ataatgtttc cagaagaaag gaaaacacat tttcagagtg cgttttatc agaggaagac   32280 aaaaatacac accctctcc agtagcttat ttttacaaag ccggcccagt gaattagaaa   32340
aacaaagcac ttggatatga ttttggaaa gcccaggtac acttattatt caaaatgcac   32400
ttttactgag tttgaaaagt ttcttttata tttaaaataa gggttcaaat atgcatattc   32460 aattttttata gtagttatct atttgcaaag catatattaa ctagtaattg ctgttaatt   32520 ttatagacat ggtagccagg gaagtatatc aatgaccta taagtatttt gacaagcaat   32580
```

```
ttacatatct gatgacctcg tatctctttt tcagcaagtc aaatgctatg taattgttcc    32640
attgtgtgtt gtataaaatg aatcaacacg gtaagaaaaa ggttagagtt attaaaataa    32700
taaactgact aaaatactca tttgaattta ttcagaatgt tcataatgct ttcaaaggac    32760
atagcagagc ttttgtggag tatccgcaca acattattta ttatctatgg actaaatcaa    32820 tttttttgaag ttgctttaaa atttaaaagc acctttgctt aatataaagc cctttaattt    32880
taactgacag atcaattctg aaactttatt ttgaaaagaa aatggggaag aatctgtgtc    32940
tttagaatta aagaaatga aaaaaataaa cccgacattc taaaaaaata gaataagaaa    33000
cctgattttt agtactaatg aaatagcggg tgacaaaata gttgtctttt tgattttgat    33060
cacaaaaaat aaactggtag tgacaggata tgatggagag atttgacatc ctggcaaatc    33120
actgtcattg attcaattat tctaattctg aataaaagct gtatacagta                33170
```

```
<210> SEQ ID NO 2
<211> LENGTH: 52
<212> TYPE: DNA
<213> ORGANISM: Homo sapiens

<400> SEQUENCE: 2
gtggcatgca ctcccacata gcccttytct gacagttccc tcagcacaca gc             52

<210> SEQ ID NO 3
<211> LENGTH: 22
<212> TYPE: RNA
<213> ORGANISM: Homo sapiens

<400> SEQUENCE: 3
cuggcccucu cugcccuucc gu                                              22

<210> SEQ ID NO 4
<211> LENGTH: 75
<212> TYPE: RNA
<213> ORGANISM: Homo sapiens

<400> SEQUENCE: 4
uggagugggg gggcaggagg ggcucaggga gaaagugcau acagccccug gcccucucug     60
cccuuccguc cccug                                                      75

<210> SEQ ID NO 5
<211> LENGTH: 22
<212> TYPE: RNA
<213> ORGANISM: Artificial sequence
<220> FEATURE:
<223> OTHER INFORMATION: Artificially synthesized micro RNA sequence

<400> SEQUENCE: 5
acggaagggc agagagggcc ag                                              22

<210> SEQ ID NO 6
<211> LENGTH: 75
<212> TYPE: RNA
<213> ORGANISM: Artificial sequence
<220> FEATURE:
<223> OTHER INFORMATION: Artificially synthesized micro RNA sequence

<400> SEQUENCE: 6
caggggacgg aagggcagag agggccaggg gcuguaugca cuuucucccu gagccccucc     60 ugcccccccca cucca                                                     75
```

```
<210> SEQ ID NO 7
<211> LENGTH: 19
<212> TYPE: RNA
<213> ORGANISM: Artificial sequence
<220> FEATURE:
<223> OTHER INFORMATION: Artificially synthesized micro RNA sequence

<400> SEQUENCE: 7
ggaagggcag agagggcca                                                19

<210> SEQ ID NO 8
<211> LENGTH: 21
<212> TYPE: RNA
<213> ORGANISM: Artificial sequence
<220> FEATURE:
<223> OTHER INFORMATION: Artificially synthesized short hairpin RNA
      sequence

<400> SEQUENCE: 8
aauaugacua ggugugguugc u                                            21

<210> SEQ ID NO 9
<211> LENGTH: 33
<212> TYPE: DNA
<213> ORGANISM: Artificial sequence
<220> FEATURE:
<223> OTHER INFORMATION: Primer

<400> SEQUENCE: 9
aggaagctta tgcagaacag tcacagcgga gtg                                33

<210> SEQ ID NO 10
<211> LENGTH: 35
<212> TYPE: DNA
<213> ORGANISM: Artificial sequence
<220> FEATURE:
<223> OTHER INFORMATION: Primer

<400> SEQUENCE: 10
aggggatcct tactgtaatc ttggccagta ttgag                              35

<210> SEQ ID NO 11
<211> LENGTH: 36
<212> TYPE: DNA
<213> ORGANISM: Artificial sequence
<220> FEATURE:
<223> OTHER INFORMATION: Primer

<400> SEQUENCE: 11
cggactagta gacaacaaca aagcagactg tgactg                             36

<210> SEQ ID NO 12
<211> LENGTH: 35
<212> TYPE: DNA
<213> ORGANISM: Artificial sequence
<220> FEATURE:
<223> OTHER INFORMATION: Primer

<400> SEQUENCE: 12
gcgacgcgtt tagagcagtt tgaacgttta ttact                              35

<210> SEQ ID NO 13
<211> LENGTH: 39
<212> TYPE: DNA
<213> ORGANISM: Artificial sequence
<220> FEATURE:
```

```
<223> OTHER INFORMATION: Primer

<400> SEQUENCE: 13
agggaactgt cagagacttt agctgtggga gtgcatgcc                              39

<210> SEQ ID NO 14
<211> LENGTH: 39
<212> TYPE: DNA
<213> ORGANISM: Artificial sequence
<220> FEATURE:
<223> OTHER INFORMATION: Primer

<400> SEQUENCE: 14
ggcatgcact cccacagcta aagtctctga cagttccct                              39

<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15
gtaaaccgag agtagcgact cc                                                22

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
gcactcccgc ttatactggg                                                   20

<210> SEQ ID NO 17
<211> LENGTH: 18
<212> TYPE: DNA
<213> ORGANISM: Artificial sequence
<220> FEATURE:
<223> OTHER INFORMATION: Primer

<400> SEQUENCE: 17
caaggacctc ggctggaa                                                     18

<210> SEQ ID NO 18
<211> LENGTH: 21
<212> TYPE: DNA
<213> ORGANISM: Artificial sequence
<220> FEATURE:
<223> OTHER INFORMATION: Primer

<400> SEQUENCE: 18
ccgggttatg ctggttgtac a                                                 21

<210> SEQ ID NO 19
<211> LENGTH: 25
<212> TYPE: DNA
<213> ORGANISM: Artificial sequence
<220> FEATURE:
<223> OTHER INFORMATION: Primer

<400> SEQUENCE: 19
gagtactacg ccaaggaggt ttaca                                             25
```

```
<210> SEQ ID NO 20
<211> LENGTH: 25
<212> TYPE: DNA
<213> ORGANISM: Artificial sequence
<220> FEATURE:
<223> OTHER INFORMATION: Primer

<400> SEQUENCE: 20
cgaacaattc tgaagtaggg tctgt                                              25

<210> SEQ ID NO 21
<211> LENGTH: 22
<212> TYPE: DNA
<213> ORGANISM: Artificial sequence
<220> FEATURE:
<223> OTHER INFORMATION: Primer

<400> SEQUENCE: 21
ggaaaacacc gagtcggaat ac                                                 22

<210> SEQ ID NO 22
<211> LENGTH: 21
<212> TYPE: DNA
<213> ORGANISM: Artificial sequence
<220> FEATURE:
<223> OTHER INFORMATION: Primer

<400> SEQUENCE: 22
gcggaaaacc ttggaggtaa t                                                  21

<210> SEQ ID NO 23
<211> LENGTH: 22
<212> TYPE: DNA
<213> ORGANISM: Artificial sequence
<220> FEATURE:
<223> OTHER INFORMATION: Primer

<400> SEQUENCE: 23
atggatgagg aaactggcaa ct                                                 22

<210> SEQ ID NO 24
<211> LENGTH: 24
<212> TYPE: DNA
<213> ORGANISM: Artificial sequence
<220> FEATURE:
<223> OTHER INFORMATION: Primer

<400> SEQUENCE: 24
gccatcgaca agaacagtgt aagt                                               24

<210> SEQ ID NO 25
<211> LENGTH: 20
<212> TYPE: DNA
<213> ORGANISM: Artificial sequence
<220> FEATURE:
<223> OTHER INFORMATION: Primer

<400> SEQUENCE: 25
gtggaggaaa tggtgtttgc                                                    20

<210> SEQ ID NO 26
<211> LENGTH: 19
<212> TYPE: DNA
<213> ORGANISM: Artificial sequence
<220> FEATURE:
<223> OTHER INFORMATION: Primer
```

```
<400> SEQUENCE: 26 gtctgcccttt ggaacttgg                                          19

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
caaggaccgg tttatttggc                                          20

<210> SEQ ID NO 28
<211> LENGTH: 21
<212> TYPE: DNA
<213> ORGANISM: Artificial sequence
<220> FEATURE:
<223> OTHER INFORMATION: Primer

<400> SEQUENCE: 28
attccctgcg aagaacacag c                                        21

<210> SEQ ID NO 29
<211> LENGTH: 18
<212> TYPE: DNA
<213> ORGANISM: Artificial sequence
<220> FEATURE:
<223> OTHER INFORMATION: Primer

<400> SEQUENCE: 29
gtgaaggtcg gagtcaac                                            18

<210> SEQ ID NO 30
<211> LENGTH: 18
<212> TYPE: DNA
<213> ORGANISM: Artificial sequence
<220> FEATURE:
<223> OTHER INFORMATION: Primer

<400> SEQUENCE: 30
gttgaggtca atgaaggg                                            18

<210> SEQ ID NO 31
<211> LENGTH: 24
<212> TYPE: RNA
<213> ORGANISM: Homo sapiens

<400> SEQUENCE: 31
agggaacugu cagagaaggg cuau                                     24

<210> SEQ ID NO 32
<211> LENGTH: 24
<212> TYPE: RNA
<213> ORGANISM: Homo sapiens

<400> SEQUENCE: 32
agggaacugu cagagacuuu agcu                                     24
```

METHOD FOR TREATING AND/OR PREVENTING MYOPIA

CROSS REFERENCE TO RELATED APPLICATION

This application claims the benefit of U.S. Provisional Application No. 62/024,078, filed on Jul. 14, 2014, the entirety of which is incorporated by reference herein.

INCORPORATION BY REFERENCE OF SEQUENCE LISTING

A sequence listing submitted as a text file via EFS-Web is incorporated herein by reference. The text file containing the sequence listing is named "0911-A52745-US_Seq_Listing.txt"; its date of creation was Mar. 10, 2015; and its size is 47,792 bytes.

TECHNICAL FIELD

The present disclosure is based on the discovery of the association between RNA interference (RNAi) and myopia and/or high myopia, and thus develops related applications of RNA interference for treatment and/or prevention, and risk assessment for myopia. The present disclosure relates to a method for treating and/or preventing myopia.

BACKGROUND

Micro RNAs (miRNAs) are noncoding, single-stranded RNA molecules about 21-33 nucleotides in length (Curr Biol 2002; 12:735-739.2.; Nature 2004; 431:350-355). In some species, a mature miRNA is complementary to the 3' untranslated region (UTR) of one or more messenger RNAs (mRNAs). The annealing of a micro RNA to its target messenger RNA causes an inhibition of protein translation, and/or cleavage of the messenger RNA. Micro RNAs are capable of regulating cell growth, differentiation, and apoptosis (Nature 2004; 431:350-355; Proceedings of the National Academy of Sciences of the United States of America 2006; 103:7024-7029; British journal of cancer 2006; 94:776-780; Science 2005; 310:1817-1821). Therefore, dysregulation of miRNAs may lead to human diseases. In this respect, several exciting researches have been focused on the role of miRNAs in cancers.

The PAX6 gene belongs to a highly conserved family of transcription factors containing the paired and homeobox DNA-binding domains. PAX6 gene is involved in the development of the central nervous system and eye development. It plays a significant role during the induction of the lens and retina differentiation, and has been considered the master gene for eye development (Exp Eye Res 2006; 83:233-234; Brain Res Bull 2008; 75:335-339). The inventors previously reported the 3' untranslated region single nucleotide polymorphism (SNP) rs662702 of the PAX6 gene is associated with extreme myopia (Invest Ophthalmol Vis Sci 2011; 52:35000-35005). In the subsequent report, the inventors proved that the preceding single nucleotide polymorphism is located in the microRNA-328 (miR-328) binding site on the PAX6 gene (Invest Ophthalmol Vis Sci. 2012 May 31; 53(6):2732-9). The functional assay suggested that the C allele of the single nucleotide polymorphism can reduce PAX6 protein levels and that significantly increases risk of myopia.

Signals which originate from the retina can be conveyed to the sclera (Vis Neurosci 2005; 22:251-261), especially those from the photoreceptors and the retinal pigment epithelium (RPE). Therefore, investigating the interaction between retinal pigment epithelium cells and scleral cells may provide more insight to the development of myopia.

However, in the past, there have been no reports about the role of micro RNA on the development of myopia, and at present, there are no reports of research related to using RNA interference as a medicament for treating and/or preventing myopia.

SUMMARY

The present disclosure provides a method for treating and/or preventing myopia, comprising administering an RNA interference (RNAi) to a subject, wherein the RNA interference is capable of counteracting another RNA interference, and the other RNA interference is an RNA interference capable of inhibiting an expression of PAX-6 gene, and the RNA interference capable of inhibiting an expression of PAX-6 gene comprises microRNA-328.

The present disclosure also provides a method for assessing whether a subject is at risk of developing myopia or high myopia.

A detailed description is given in the following embodiments with reference to the accompanying drawings.

BRIEF DESCRIPTION OF DRAWINGS

The present disclosure can be more fully understood by reading the subsequent detailed description and examples with references made to the accompanying drawings, wherein:

FIG. 2A shows a schematic diagram of a microRNA-328 binding site in the PAX6 3' untranslated region;

Two reporter constructs were constructed, one with three copies of the risk C allele of the 3' untranslated region SNP rs662702 while the other with three copies of the protective T allele. Constructs were co-transfected with microRNA-328 mimic into retinal pigment epithelium cells. After 24-hour incubation, the luciferase activity was measured. pEGFP plasmids were also co-transfected into cells, and the GFP signal was used as internal control. Data are means±standard deviation of three experiments, and * means p value<0.05.

Figure 4A:
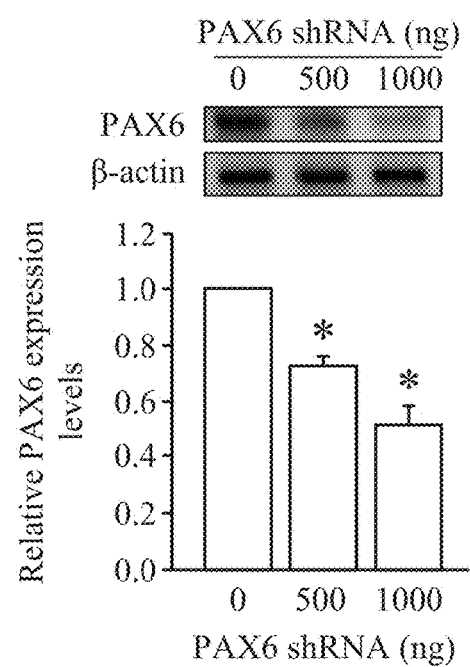

FIG. 4A shows that short hairpin RNA against PAX6 dose dependently knocked down PAX6 expression in retinal pigment epithelium cells.

Figure 4B:
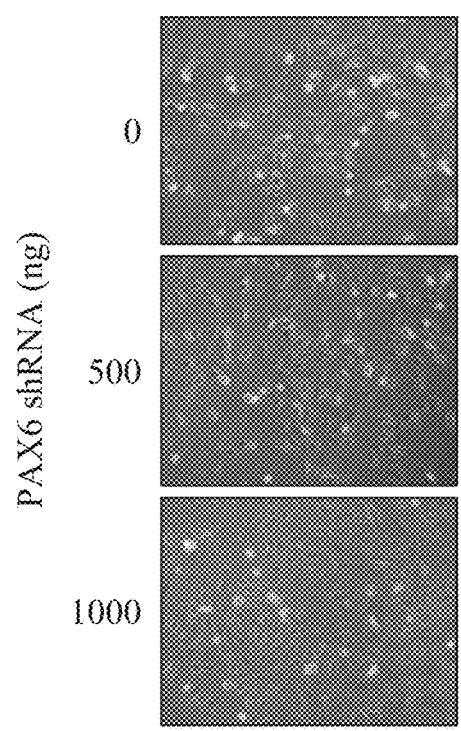
Figure 4C:
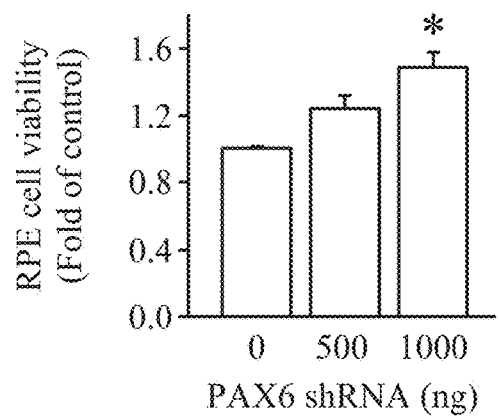

FIGS. 4B and 4C respectively show PAX6 knockdown in retinal pigment epithelium cells enhancing retinal pigment epithelium cell proliferation observed with a microscope and demonstrated by the WST-1 assay.

Figure 4D:
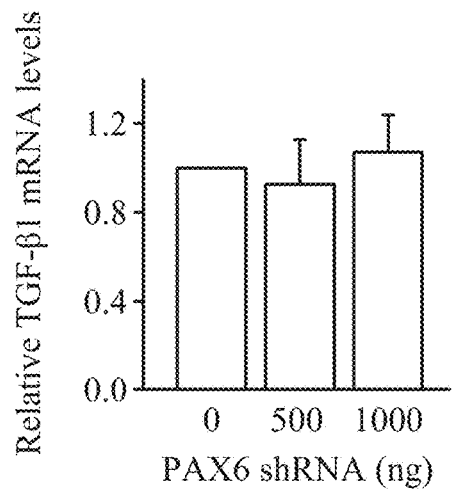
Figure 4E:
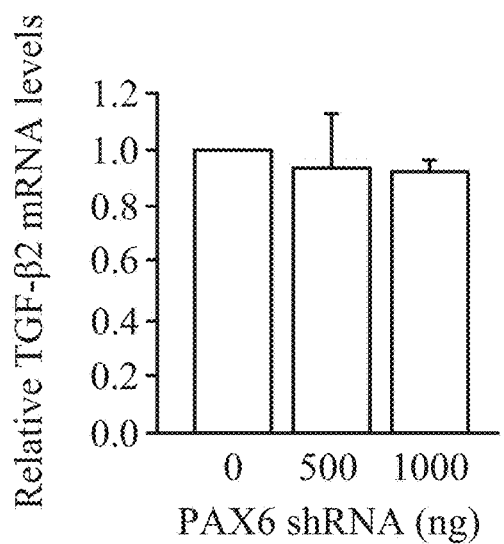
Figure 4F:
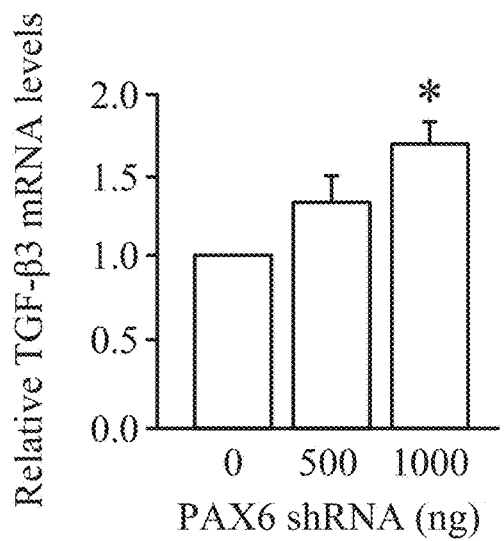

FIGS. 4D-4F show that knocked-down PAX6 induces TGF-β3 expression. After cells were transfected with short hairpin RNA against PAX6 for 24 hours, the relative mRNA levels of PAX6, TGF-β1, TGF-β2, and TGF-β3 were analyzed by the quantitative polymerase chain reactions. The protein level of PAX6 was analyzed by immunoblot. Data are means±standard deviation of three experiments, and * means p value<0.05.

Figure 5A:
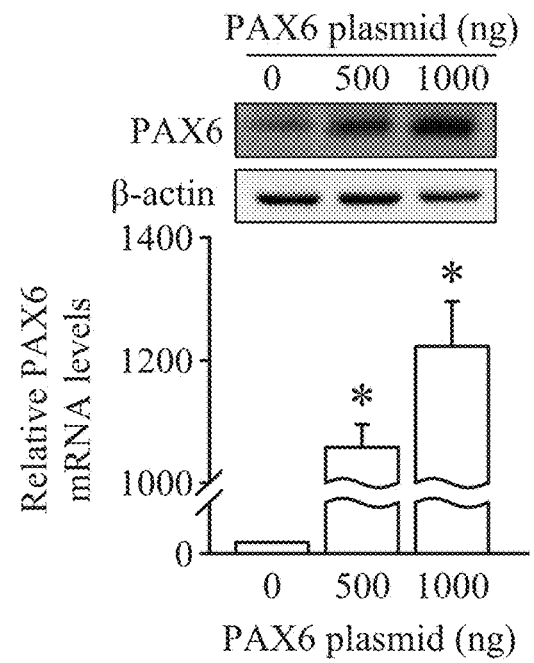
Figure 5B:
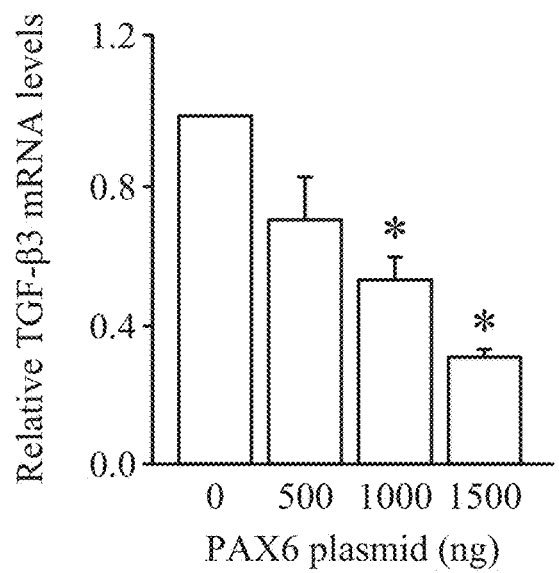

FIGS. 5A and 5B respectively show overexpression of PAX6 in retinal pigment epithelium cells and repressed TGF-β3 expression due to overexpression of PAX6 in retinal pigment epithelium cells. After cells were transfected with dose course of pEGFP-PAX6 plasmid for 24 hours, the relative mRNA levels of PAX6 and TGF-β3 were respectively analyzed by using quantitative polymerase chain reaction. The protein level of PAX6 was analyzed by using western blotting assay. Data are means±standard deviation of three experiments, and * means p value<0.05.

Figure 6A:
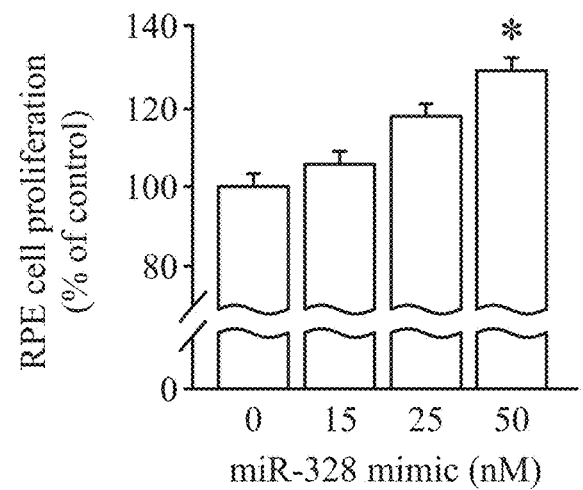
Figure 6B:
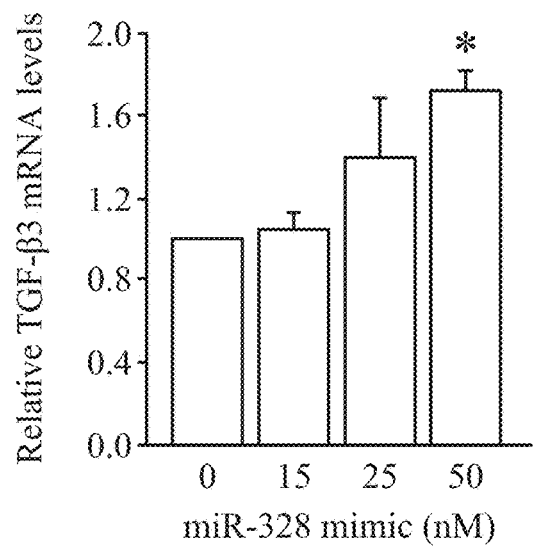

FIGS. 6A and 6B respectively show that microRNA-328 enhances retinal pigment epithelium cell proliferation and microRNA-328 increases TGF-β3 expression. After cells were transfected with microRNA-328 mimic for 24 hours, the relative mRNA levels of TGF-β3 were measured by quantitative polymerase chain reactions. Cell viability was assessed by the WST-1 assay. Data are means±standard deviation of three experiments, and * means p value<0.05.

Figure 7A:
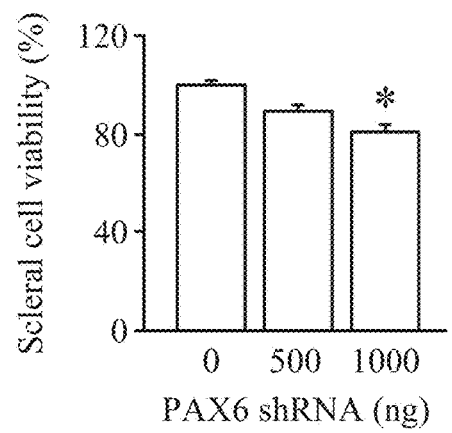
Figure 7B:
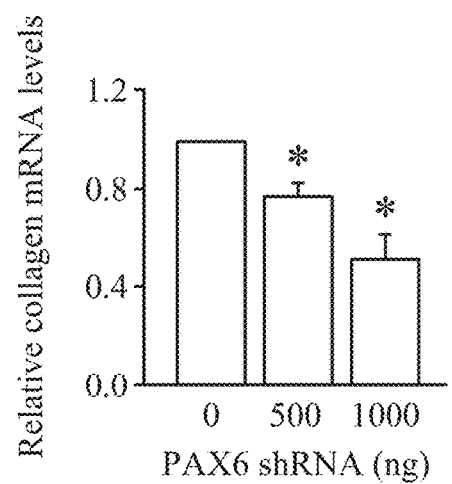
Figure 7C:
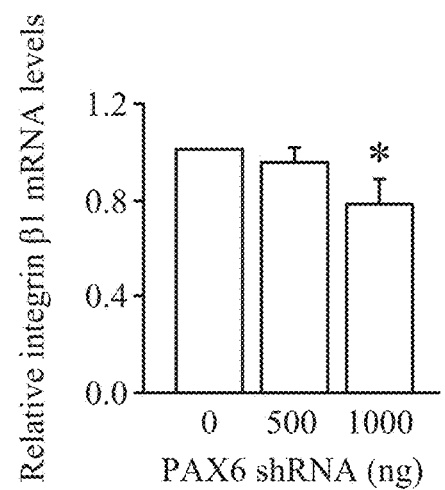
Figure 7D:
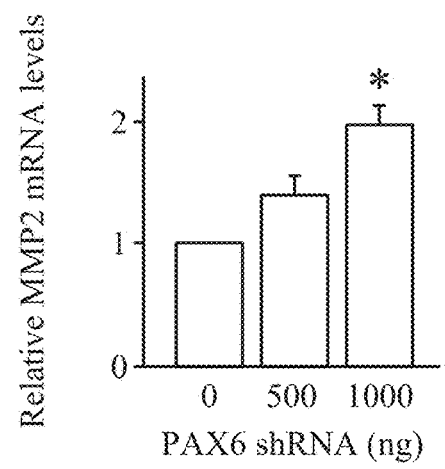
Figure 7E:
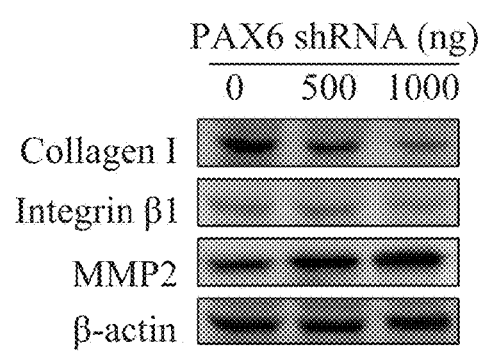

FIGS. 7A-7E respectively show that down-regulated PAX6 in retinal pigment epithelium cells influences scleral cell viability (FIG. 7A), mRNA levels of collagen I, integrin β1 and matrix metalloproteinase 2 (FIGS. 7B-7D), and protein levels of collagen I, integrin β1 and matrix metalloproteinase 2 (FIG. 7E). After REP cells were transfected with short hairpin RNA against PAX6 for 24 hours, the conditioned medium was collected and added to the scleral cells. The relative mRNA and protein levels in scleral cells were measured by the quantitative polymerase chains reactions and the immunoblots, respectively. Respective cell viability was studied by the WST-1 assay. Data are means±standard deviation of three experiments, and * means p value<0.05.

Figure 8A:
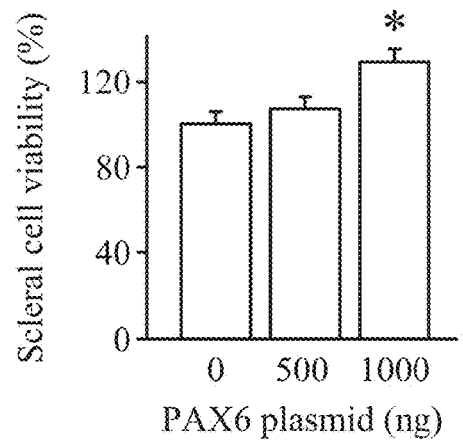
Figure 8B:
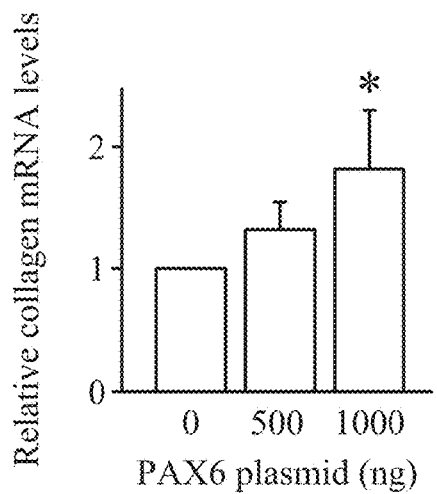
Figure 8C:
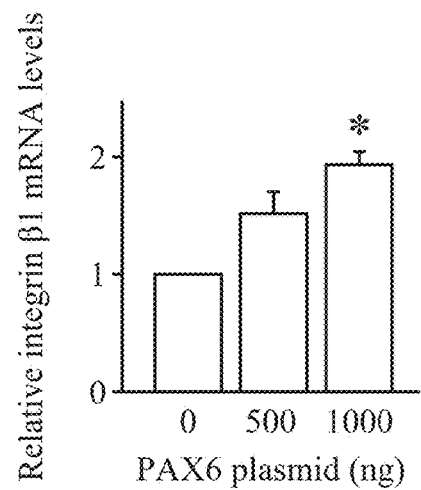
Figure 8D:
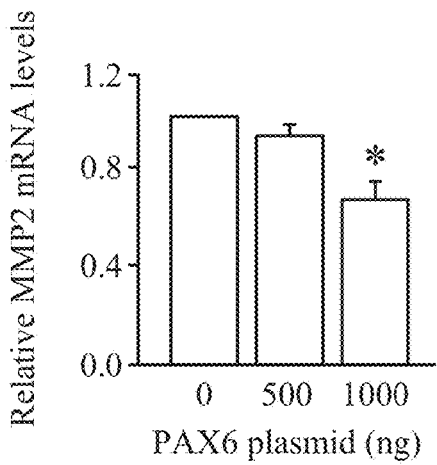
Figure 8E:
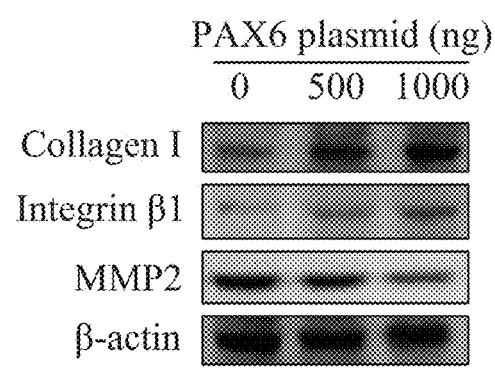

FIGS. 8A-8E respectively show that overexpression of PAX6 influences scleral cell viability (FIG. 8A), mRNA levels of collagen I, integrin β1 and matrix metalloproteinase 2 (FIGS. 8B-8D), and protein levels of collagen I, integrin β1 and matrix metalloproteinase 2 (FIG. 8E). After cells were respectively transfected with plasmid carried PAX6 gene for 24 hours, the conditioned medium was collected and added to the scleral cells. The relative mRNA and protein levels in scleral cells were measured by the quantitative polymerase chain reactions and the immunoblots, respectively. Respective cell viability was studied by the WST-1 assay. Data are means±standard deviation of three experiments, and * means p value<0.05.

Figure 9A:
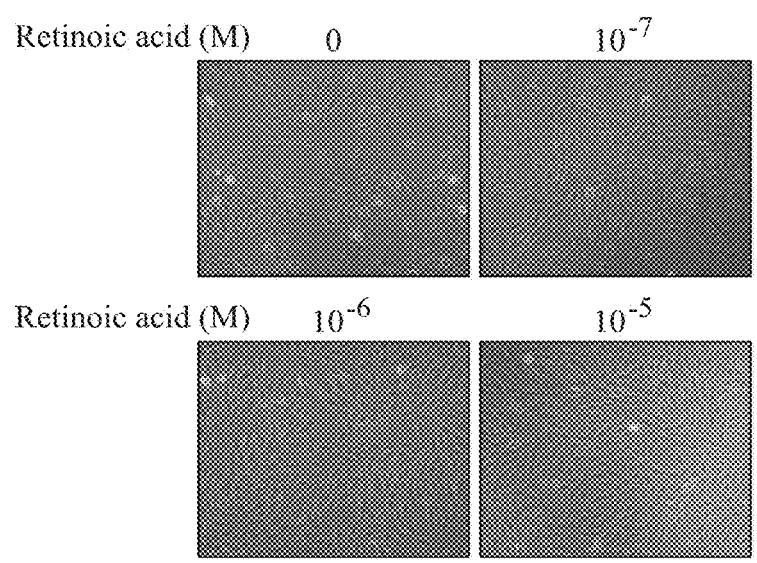
Figure 9B:
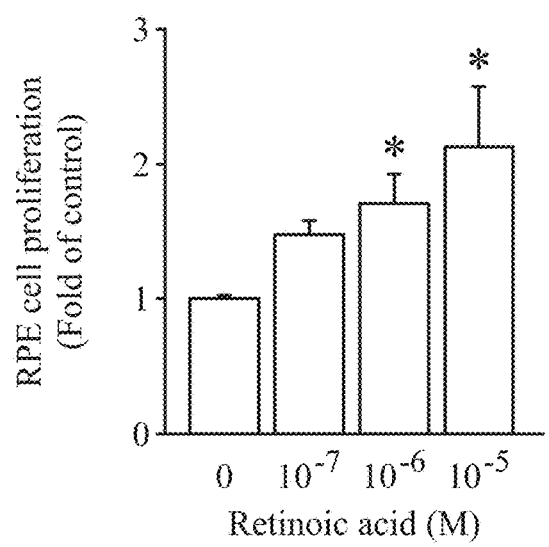

FIGS. 9A and 9B respectively show the results of observing retinal pigment epithelium cells treated with retinoic acid with a microscope and analyzing retinal pigment epithelium cells treated with retinoic acid by WST-1 assay. The results show that retinoic acid enhances retinal pigment epithelium cell proliferation. After cells were treated with retinoic acid, cell viability was observed by microscope imaging and measured by the WST-1 assay. Data are means±standard deviation of three experiments, and * means p value<0.05.

Figure 9C:
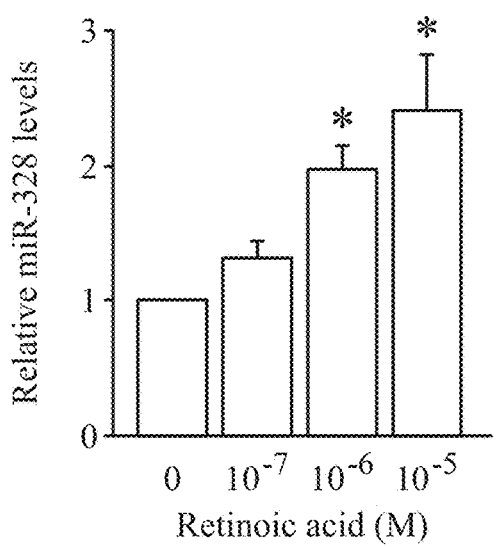
Figure 9D:
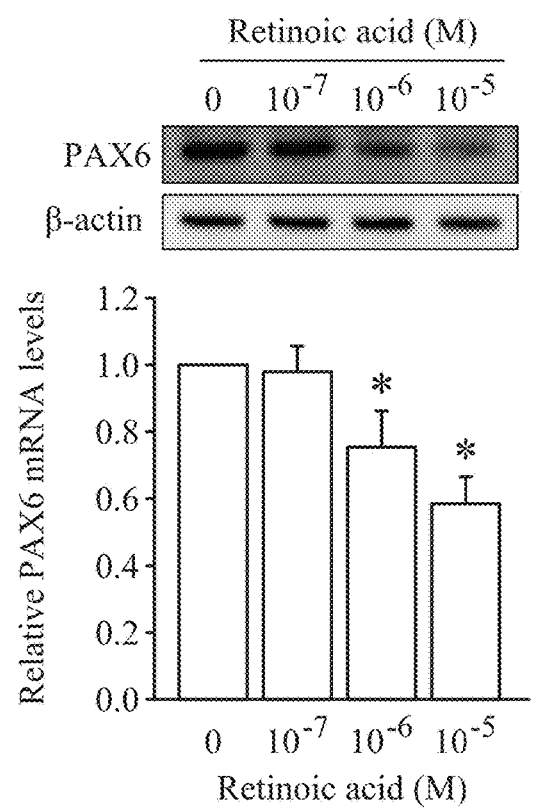

FIGS. 9C and 9D respectively show that retinoic acid induce microRNA-328 expression and retinoic acid decrease micro PAX6 expression. After cells were treated with retinoic acid for 24 hours, the relative mRNA levels of PAX6 and microRNA-328 were measured by the quantitative polymerase chain reactions. The protein level of PAX6 was measured by immunoblot. Data are means±standard deviation of three experiments, and * means p value<0.05.

Figure 10A:
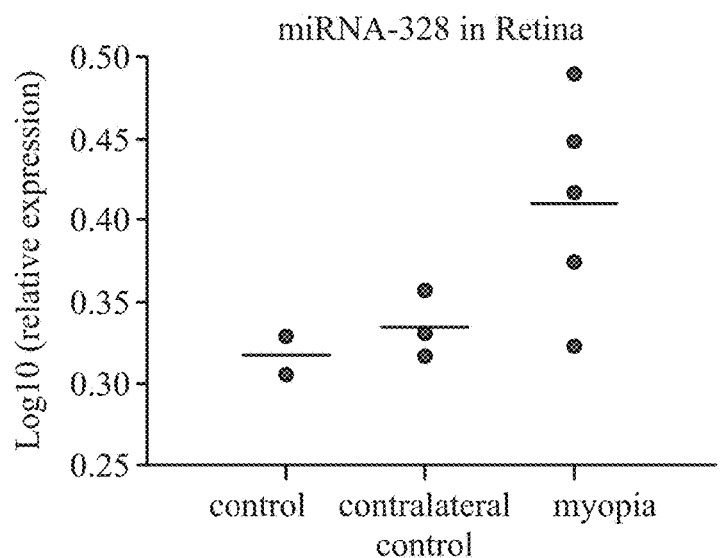

FIG. 10A shows microRNA-328 expression level in the retinas: for the normal mouse, (control group), for the normal eye of the experimental mouse (control group for the opposite side eye) and the myopic eye of the experimental mouse.

Figure 10B:
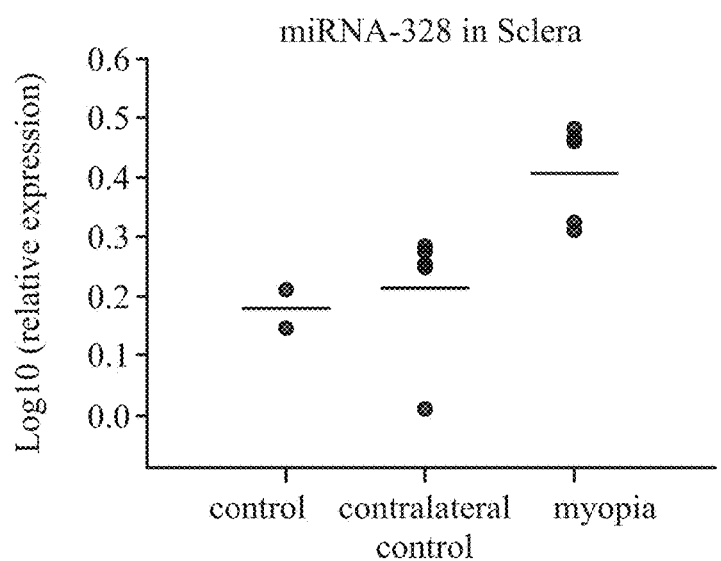

FIG. 10B shows microRNA-328 expression level in the retinas: for the normal mouse, (control group), for the normal eye of the experimental mouse (control group for the opposite side eye) and the myopic eye of the experimental mouse.

Figure 11A:
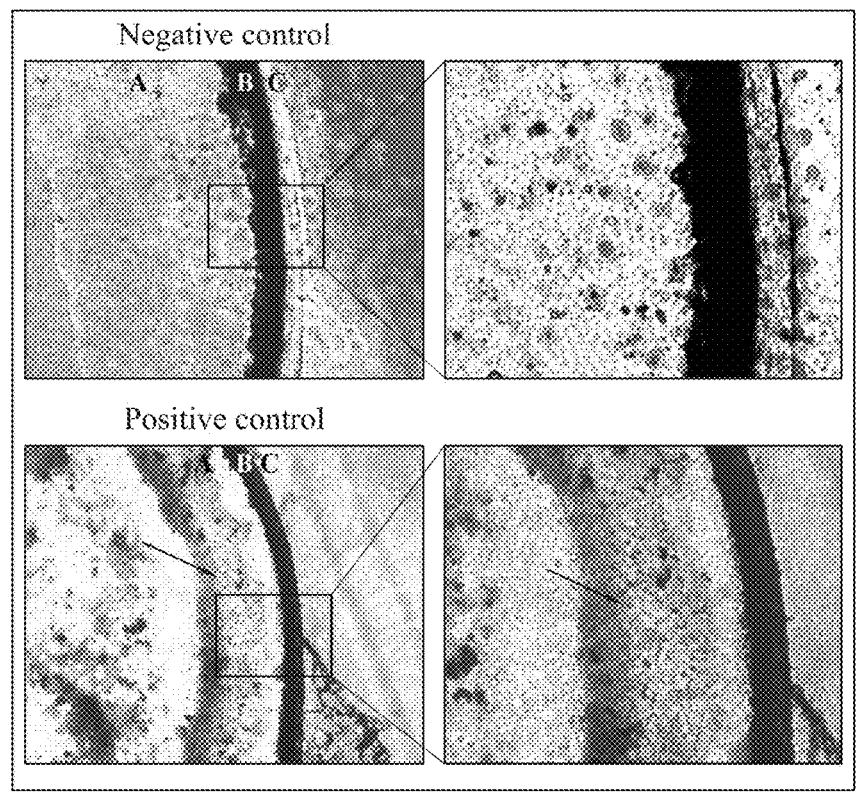
Figure 11B:
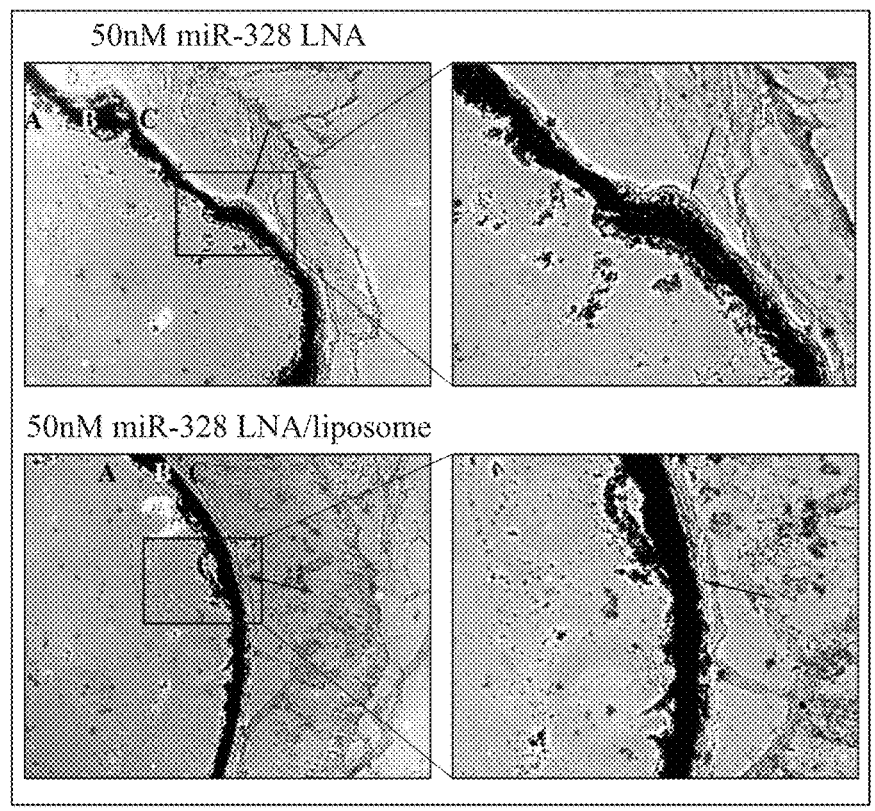

FIGS. 11A and 11B show the results for administering locked nucleic acid modified antisense for microRNA-328 in the form of an eye drop to the eyes of the mouse and then performing sectioning and in situ hybridization on the eyes of the mouse. FIG. 11A shows the results of the negative control and the positive control, and FIG. 11B shows the results of the results of the groups respectively treated with the eye drop containing non-encapsulated locked nucleic acid modified antisense for microRNA-328 and eye drop containing encapsulated locked nucleic acid modified antisense for microRNA-328. In FIGS. 11A and 11B, the photographs on the left were 200 times magnification; the photographs on the right magnify the rectangular frame in the photographs on the left. The results show that locked nucleic acid modified antisense for microRNA-328 can reach the retina and the scleral (shown in purple (indicated by an arrow mark)). A: Retina; B: Choroid; C: Scleral.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure is based on the discovery of the relation between RNA interference (RNAi) and myopia and/or high myopia, and thus develops related applications of RNA interference for treatment and/or prevention, and risk assessment for myopia.

At present, it is known that PAX6 gene (SEQ ID NO. 1) regulating expressions of the downstream genes may relate to the development of myopia, and in the experiments of the present disclosure, it is proven that microRNA-328 exists in animal ocular tissues, and exists in the sclera and the retina of myopic mice. Moreover, the experiments of the present disclosure prove that microRNA-328 can bind to 3' untranslated region of the PAX6 gene, and confirm that microRNA-328 can regulate mRNA of PAX6 to decrease both the amount thereof and the protein expression amount of PAX6.

Furthermore, in the experiments of the present disclosure, it is proven that risk C allele of the single nucleotide polymorphism (SNP) rs662702 (SEQ ID NO. 2) located on the PAX6 3' untranslated region, as compared to its protective T allele, has a higher sensitivity to microRNA-328. Namely, the single nucleotide polymorphism rs662702 located on the 3' untranslated region substantiality influences the binding ability of microRNA-328 to the PAX6 3' untranslated region and results in different danger level of suffering myopia within individuals.

In addition, during the formation of myopia, the retinal pigment epithelium will proliferate. Moreover, previous studies indicate that an increase of TGF-β was an important factor in the retinoscleral signaling pathway during myopia development (J Exp Eye Res 2009; 88:458-466). In the present disclosure, it is confirmed that in retinal pigment epithelium cells, by an RNA interference method can reduce PAX6 expressions in a dose-dependent manner, and the reduction of PAX6 significantly enhanced retinal pigment epithelium cell proliferation and significantly enhanced TGF-β3 expression. Furthermore, in the present disclosure, it is also confirmed that microRNA-328 mimic can dose-dependently enhance retinal pigment epithelium cell proliferation and induce TGF-β3 expression in retinal pigment epithelium cells.

Moreover, at present it is known that scleral thinning, reduced scleral collagen I accumulation, decreased integrin β1 subunit expression, and increased matrix metalloproteinase 2 (MMP2) are important changes in the development of myopia (Exp Eye Res 2006; 82:185-200; Invest Ophthalmol Vis Sci 2006; 47:4674-4682; Exp Eye Res 1996; 63:369-381. Invest Ophthalmol Vis Sci 2001; 42:1153-1159; Invest Ophthalmol Vis Sci 2002; 43:2067-2075), and in the present disclosure, reducing PAX6 expression in the sclera cells by an RNA interference method can result in significant decreases of collagen I and integrin β1 levels but an increase of matrix metalloproteinase 2 expression levels.

According to the foregoing, the present disclosure has clearly proved that RNA interference, such as microRNA-328, etc. can reduce the expression level of PAX6, and thus cause myopia development factors go toward a condition to develop myopia. Therefore, in the present disclosure, a concept is proposed, and in the concept, the RNA interference related to myopia development in the body mentioned above is counteracted by using another RNA interference to achieve the effects of treating and preventing myopia.

Therefore, in one aspect of the present disclosure, the present disclosure provides a method for treating and/or preventing myopia. The method for treating and/or preventing myopia may comprise administering an RNA interference (RNAi) to a subject, but it is not limited thereto. The foregoing RNA interference is capable of counteracting another RNA interference.

The subject may comprise a mammal, such as mouse, rat, rabbit, dog, cat, monkey, orangutan, human, etc. but it is not limited thereto. In one embodiment, the subject is a human. In another embodiment, the subject is a mouse. Moreover, the subject may be a subject suffering from myopia or a normal subject which has the possibility of suffering from myopia.

The other RNA interference mentioned above may be an RNA interference capable of inhibiting an expression of PAX-6 gene. In one embodiment, the preceding RNA interference capable of inhibiting an expression of PAX-6 gene may comprise microRNA-328, but it is not limited thereto. In an exemplificative embodiment, the preceding RNA interference capable of inhibiting an expression of PAX-6 gene is microRNA-328.

As mentioned in the present disclosure, "microRNA-328" refers to a mature form of microRNA-328 or a precursor of microRNA-328 (comprising pre-microRNA-328 and pri-microRNA-328). In one embodiment, microRNA-328 may comprise an original human microRNA-328 (the sequence of the original human microRNA-328 is CUGGCCCUCU-CUGCCCUUCCGU (SEQ ID NO. 3)), a modified human microRNA-328 such as a precursor of human microRNA-328 (for example, human pre-microRNA-328 (the sequence thereof is UGGAGUGGGGGGGCAGGAGGGGCUCA-GGGAGAAAGUGCAUACAGCCCCUGG CCCUCU-CUGCCCUUCCGUCCCCUG (SEQ ID NO. 4)) and human pri-microRNA-328).

Furthermore, in the preceding embodiment in which the RNA interference capable of inhibiting an expression of PAX-6 gene may comprise microRNA-328, the foregoing RNA interference capable of inhibiting an expression of PAX-6 gene may comprise an antisense RNA for counteracting the microRNA-328, and the sequence of the antisense RNA for counteracting the microRNA-328 may comprise at least a part of the complementary sequence for the microRNA-328.

In one embodiment, the sequence of the preceding antisense RNA for counteracting the microRNA-328 may comprise SEQ ID NO. 5 (the complementary sequence for SEQ ID NO. 3) or SEQ ID NO. 6 (the complementary sequence for SEQ ID NO. 4). In another embodiment, the sequence of the preceding antisense RNA for counteracting the microRNA-328 may comprise SEQ ID NO. 7. In an exemplificative embodiment, the sequence of the preceding antisense RNA for counteracting the microRNA-328 is SEQ ID NO. 7.

In addition, the foregoing antisense RNA for counteracting the microRNA-328 may be composed of non-modified RNA or comprise at least one chemically modified nucleic acid.

Generally, antisense oligonucleotides have to possess the following characteristics, and thus can be applied to the use of medical therapy 1. capable of resisting exonucleases to increase stability;
2. having high solubility; and
3. having good hybridization ability.

Figure 1:
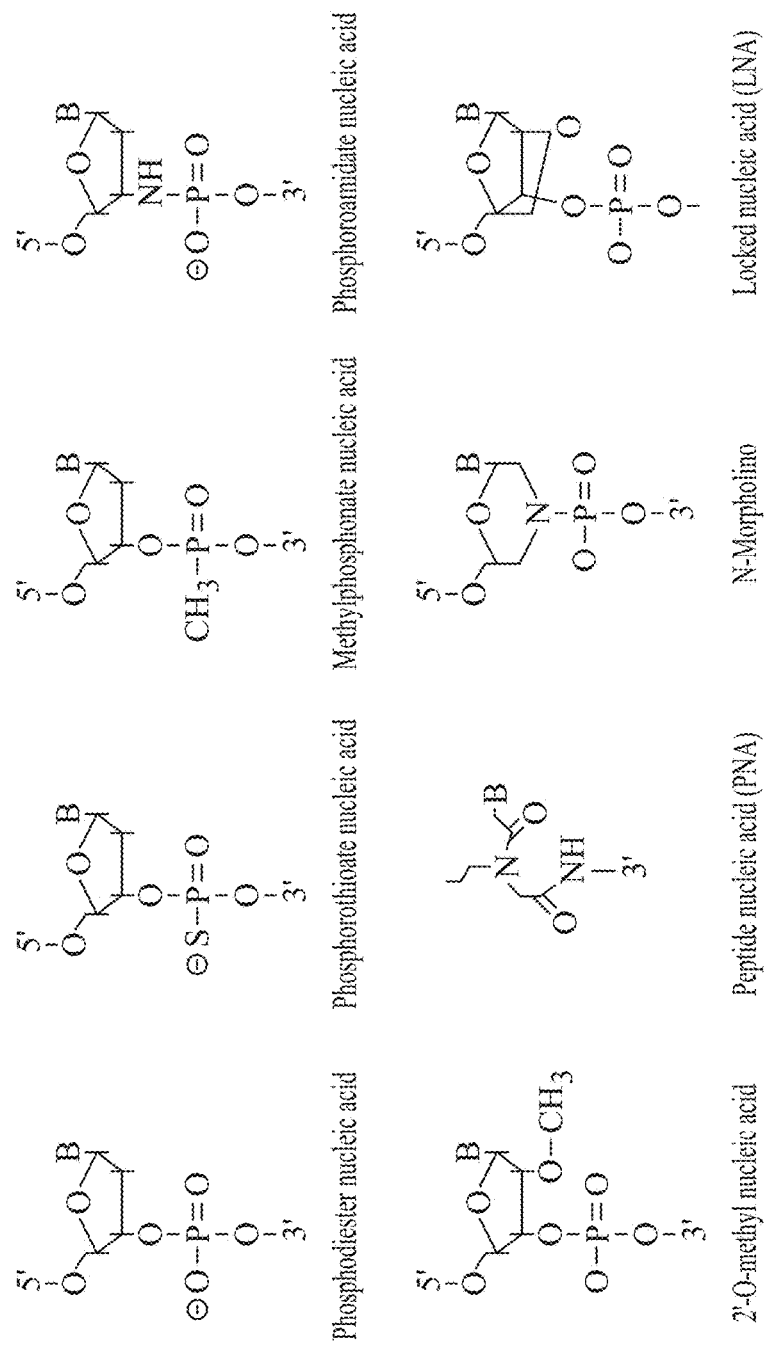
FIG. 1 shows different types of chemically modified nucleic acids.

In order to increase the stability, solubility and hybridization ability of an RNA interference, at present, RNA interference is formed by chemically modified nucleic acids to promote medical therapy applications thereof. The types of chemically modified nucleic acids may be referred to in FIG. 1 (from Kausch et al. (2002) J Urol. 168(1):239-247), and chemically modified nucleic acids can be classified into three types based on the chemical modification thereto:

(1) With modification of phosphate group, such as phosphodiester nucleic acid, phosphorothioate nucleic acid, methylphosphonate nucleic acid and phosphoroamidate nucleic acid;

(2) With modification of the oxygen linked by 2' carbon of pentose, such as 2'-O -methyl nucleic acid and locked nucleic acid (LNA); and (3) With modification of 3' carbon of pentose, such as peptide nucleic acid (PNA) and N-Morpholino.

Therefore, in the embodiment mentioned above, chemically modified nucleic acids which can form an antisense RNA for counteracting the microRNA-328 may comprise, but are not limited to phosphodiester nucleic acid, phosphorothioate nucleic acid, methylphosphonate nucleic acid, phosphoroamidate nucleic acid, 2'-O-methyl nucleic acid, peptide nucleic acid (PNA), N-Morpholino or locked nucleic acid (LNA).

In addition, the RNA interference capable of counteracting another RNA interference may be formulated alone to form a medicament or may be formulated with a pharmaceutically acceptable carrier to form a medicament. In an exemplificative embodiment, the medicament mentioned above is in the form of an eye drop.

The pharmaceutically acceptable carrier may comprise a nanoparticle, but it is not limited thereto. Nanoparticles are defined as particulate dispersions or solid particles with a size in the range of 10-1000 nm. Nanoparticles can be prepared from a variety of materials such as lipids, proteins, polysaccharides and synthetic polymers. Depending upon the method of preparation, nanoparticles, nanospheres or nanocapsules can be obtained. Nanocapsules are systems in which the agent is confined to a cavity surrounded by a unique polymer membrane, while nanospheres are matrix systems in which the drug is physically and uniformly dispersed. Nanoparticles have been prepared most frequently by three methods: (1) dispersion of preformed polymers; (2) polymerization of monomers; and (3) ionic gelation or coacervation of hydrophilic polymers. However, other methods such as supercritical fluid technology and particle replication in non-wetting templates (PRINT) have also been described in the literature for production of nanoparticles.

Examples of the foregoing nanoparticle may comprise, but are not limited to, a liposome, a micelle, a metal nanoparticle and a polymer nanoparticle.

In one embodiment, the nanoparticle mentioned above is a liposome, and the foregoing RNA interference capable of counteracting another RNA interference is encapsulated in the liposome. Moreover, in this embodiment, the preceding medicament may be in the form of an eye drop.

The pharmaceutically acceptable carrier mentioned above may also comprise, but is not limited to, a solvent, a dispersion medium, a coating, an antibacterial and antifungal agent, and an isotonic and absorption delaying agent, etc. and they are compatible to pharmaceutical administration. The pharmaceutical composition can be formulated into dosage forms for different administration routes utilizing conventional methods.

Furthermore, the pharmaceutically acceptable salt may comprise, but is not limited to, inorganic cation salts including alkali metal salts such as sodium salt, potassium salt or amine salt, alkaline-earth metal salt such as magnesium salt or calcium salt, the salt containing bivalent or quadrivalent cation such as zinc salt, aluminum salt or zirconium salt. In addition, the pharmaceutically acceptable salt may also comprise organic salt including dicyclohexylamine salt, methyl-D-glucamine, and amino acid salt such as arginine, lysine, histidine, or glutamine.

The medicament prepared from the present disclosure may be administered orally, parentally, via an inhalation spray or via an implanted reservoir. The parental method may comprise eye drop, subcutaneous, intracutaneous, intravenous, intramuscular, intraarticular, intraarterial, intrasynovial, intrasternal, intrathecal, and intralesional, as well as infusion techniques.

An oral composition can comprise, but is not limited to, tablets, capsules, emulsions and aqueous suspensions, dispersions and solutions.

EXAMPLES

A. Material and method
Material

The Luciferase Assay System and cloning kits were purchased from Promega Corporation (Madison, Wis., USA). Anti-PAX6, anti-collagen I, anti-integrin β, and anti-matrix metalloproteinase 2 (MMP2) antibodies were purchased from GeneTex Inc (Irvine, Calif., USA). Anti-β-actin antibody, Enhanced Chemiluminescence (ECL) solution, and WST-1 were purchased from Millipore (Billerica, Mass., USA). Trizol® reagent, secondary antibodies and Lipofectamine were purchased from Invitrogen (Carlsbad, Calif., USA). SYBR® Green PCR Master Mix, MultiScribe™ Reverse Transcriptase Kit, TaqMan® microRNA-328 and U44 Assays, and microRNA-328 mimic were purchased from Applied Biosystems (Carlsbad, Calif., USA). Primer sets were synthesized by Mission Biotech (Nankang, Taiwan). Anti-PAX6 shRNA was purchased from the National RNAi Core Facility (Nankang, Taiwan). The ARPE-19 cell line was purchased from ATCC (Manassas, Va., USA). The cell culture-related reagents were purchased from GIBCO-BRL (Grand Island, N.Y., USA). Unless otherwise specified, all other reagents were of analytical grade.

Method

1. Cell Culture, Treatments and Transfection

The human retinal pigment epithelium (RPE) cell line, ARPE-19, was grown in DMEM/F12 medium with 1% Penicillin/Streptomycin and 10% heat-inactivated fetal bovine serum (FBS) at 37° C. in a humidified atmosphere of 95% air/5% $CO_2$. Cells below passage 20 were used in all experiments. To conduct the transfection experiments, retinal pigment epithelium cells were seeded into a 12-well plate at a density of $1 \times 10^5$ cells/well. After achieving 70% confluence in a well, a short hairpin RNA (shRNA) as control or a short hairpin RNA against PAX6 and pEGFP-N3, or a plasmid with PAX6 gene were respectively transfected with Lipofectamine 2000 (Invitrogen). After 24-hour incubation, retinal pigment epithelium cells were lysed for further study.

2. RNA Isolation and Quantitative Real-Time Polymerase Chain Reaction (PCR)

Extraction of total RNA from cultured cells was carried out using Trizol®. RNA purity was checked using A260/A280 readings. cDNA was synthesized from 1 μg total RNA using random primers and the MultiScribe™ Reverse Transcriptase Kit. cDNA of microRNA-328 was synthesized with TaqMan® MicroRNA Assay. The cDNA was diluted by a ratio of 1:30 with PCR grade water and then stored at −20° C.

For quantitative real-time PCR, specific primers were designed, and the details are listed in Table 1. Gene expression level was quantified on an ABI 7500 real-time PCR machine (Applied Biosystems) with pre-optimized conditions. Each polymerase chain reaction was performed in duplicate using 5 μl 2×SYBR Green PCR Master Mix, 0.2 μL primer sets, 1 μL cDNA, and 3.6 μl nucleotide-free $H_2O$ to yield a 10 μL of total reaction volume. The expression level of microRNA-328 was normalized to that of U44 as the internal control for microRNA-328 by using the equation of $\log_{10}(2^{-\Delta Ct})$, where $\Delta Ct = (Ct_{microRNA-328} - C_{TU44})$. The relative expression level of other genes was normalized to the level of the housekeeping gene GAPDH.

TABLE 1

Primer Sequences for quantitative real-time polymerase chain reaction

| Primer | Sequence |
|---|---|
| *For cloning PAX6 full length cDNA* | |
| PAX6-clone-F | AGGAAGCTTATGCAGAACAGTCACAGCGGAGTG (SEQ ID NO. 9) |
| PAX6-clone-R | AGGGGATCCTTACTGTAATCTTGGCCAGTATTGAG (SEQ ID NO. 10) |
| *For PAX6 3' untranslated region reporter assay* | |
| PAX6-3UTR-F | CGGACTAGTAGACAACAACAAAGCAGACTGTGACTG (SEQ ID NO. 11) |
| PAX6-3UTR-R | GCGACGCGTTTAGAGCAGTTTGAACGTTTATTACT (SEQ ID NO. 12) |
| PAX6-3UTR-mut-F | AGGGAACTGTCAGAGACTTTAGCTGTGGGAGTGCATGCC (SEQ ID NO. 13) |
| PAX6-3UTR-mut-R | GGCATGCACTCCCACAGCTAAAGTCTCTGACAGTTCCCT (SEQ ID NO. 14) |
| *For gene expression* | |
| Pax6-F | GTAAACCGAGAGTAGCGACTCC (SEQ ID NO. 15) |
| Pax6-R | GCACTCCCGCTTATACTGGG (SEQ ID NO. 16) |
| TGF-β1-F | CAAGGACCTCGGCTGGAA (SEQ ID NO. 17) |
| TGF-β1-R | CCGGGTTATGCTGGTTGTACA (SEQ ID NO. 18) |
| TGF-β2-F | GAGTACTACGCCAAGGAGGTTTACA (SEQ ID NO. 19) |
| TGF-β2-R | CGAACAATTCTGAAGTAGGGTCTGT (SEQ ID NO. 20) |
| TGF-β3-F | GGAAAACACCGAGTCGGAATAC (SEQ ID NO. 21) |
| TGF-β3-F | GCGGAAAACCTTGGAGGTAAT (SEQ ID NO. 22) |
| Collagen I-F | ATGGATGAGGAAACTGGCAACT (SEQ ID NO. 23) |
| Collagen I-R | GCCATCGACAAGAACAGTGTAAGT (SEQ ID NO. 24) |
| Integrin β1-F | GTGGAGGAAATGGTGTTTGC (SEQ ID NO. 25) |
| Integrin β1-R | GTCTGCCCTTGGAACTTGG (SEQ ID NO. 26) |
| MMP2-F | CAAGGACCGGTTTATTTGGC (SEQ ID NO. 27) |
| MMP2-R | ATTCCCTGCGAAGAACACAGC (SEQ ID NO. 28) |
| GAPDH-F | GTGAAGGTCGGAGTCAAC (SEQ ID NO. 29) |
| GAPDH-R | GTTGAGGTCAATGAAGGG (SEQ ID NO. 30) |

3. Immunoblot Analysis

Cells were harvested in RIPA buffer (1% Nonidet P-40, 0.5% deoxycholate, 0.1% SDS in PBS) containing protease inhibitor cocktail (Calbiochem) and centrifuged at 12,000 rpm for 10 minutes at 4° C. The supernatant was used as total cell lysate. Lysates (20 µg) were denatured in 2% SDS, 10 mM dithiothreitol, 60 mM Tris-HCl (pH 6.8), and 0.1% bromophenol blue, and loaded onto a 10% polyacrylamide/SDS gel. Then, the separated proteins were transferred onto a PVDF membrane. The membrane was blocked for 1 hour at room temperature in PBS containing 5% non-fat dry milk and incubated overnight at 4° C. in PBS-T containing the primary antibody. The membrane was washed in PBS-T, incubated with the secondary antibody conjugated to horseradish peroxidase for 1 hour at room temperature, and then washed in PBS-T. The ECL non-radioactive detection system was used to detect the antibody-protein complexes by photographing with a Bio-Rad ChemiDoc XRS System.

4. Construction of the PAX6 3' Untranslated Region Reporter Plasmid and Mutagenesis Polymerase chain reaction was performed using sets of primers specific for the PAX6 3' untranslated region listed in Table 1, of which the forward primer was SpeI-site-linked and the reverse primer was MluI-site-linked. Retinal pigment epithelium genomic DNA was used as the template. The 1500-bp polymerase chain reaction products were digested with SpeI and MluI and cloned downstream of the luciferase gene in the pMIR-REPORT luciferase vector (Ambion). This vector was sequenced and named pMIR-PAX6-3'UTR. Site-directed mutagenesis of the microRNA-328 target site in the PAX6 3' untranslated region was carried out using the QuikChange® Site-Directed Mutagenesis Kit (Stratagene, Heidelberg, Germany) and the vector named pMIR-PAX6-3UTR-mutant. For reporter assays, the cells were transiently transfected with wild-type (pMIR-PAX6-3'UTR) or mutant (pMIR-PAX6-3'UTR-mutant) reporter plasmids and microRNA-328 mimic by using Lipofectamine 2000 (Invitrogen). The pEGFP plasmids were co-transfected and acted as the internal control. 24 hours after the transfection, the reporter assay was performed using the Luciferase Assay System (Promega).

5. Construction of Full-Length PAX6 cDNA

The full-length cDNA of PAX6 (NM_000280) was generated by PCR amplification using the primers listed in Table 1. The following thermal profile was used for the PCR amplification of cDNA (500 ng) in a GeneAmp PCR system 9700 (Applied Biosystems): an initial denaturation step at 95° C. for 5 minutes; followed by 40 cycles of 94° C. for 1 minute; 59° C. for 1 minute and 72° C. for 1 minute, with a final extension at 72° C. for 10 minutes. The polymerase chain reaction products were analyzed by agarose gel electrophoresis. All the polymerase chain reaction products were cloned into pGEM-T Easy vectors (Promega Corporation). After HindIII/BamHI digestion, PAX6 cDNA was cloned into pEGFP-N3 to form a construct of pEGFP-PAX6. All the sequences of constructs were confirmed by DNA sequencing.

6. Cell Proliferation Assay

Cell proliferation was determined by using microscope images and the WST-1 cell proliferation assay (Millipore) according to the manufacturer's instructions. Briefly, the cells were seeded in triplicate in 12-well plates at $10^5$ cells per well. After cells were transfected with microRNA-328 mimic or PAX6 short hairpin RNA for 24 hours, images were obtained from a Nikon inverted microscope (Nikon Instruments Inc., Melville, N.Y.). Then, cells were further incubated with WST-1 reagent and medium at a ratio of 1:10 for 4 hours, and the absorption at 440 nm and 650 nm of the samples (with a background control as a blank) were measured using a microplate reader.

7. Preparation of Conditioned Medium and Treatment

To collect conditioned medium, retinal pigment epithelium cells were seeded into a 12-well plate at a density of $1\times10^5$ cells/well. After achieving 70% confluence in a well, scrambled short hairpin RNA or short hairpin RNA against PAX6 and pEGFP-N3 plasmid or plasmid carrying PAX6 gene were respectively transfected with Lipofectamine 2000 (Invitrogen). After 24 hours, the medium (called conditioned medium) was collected. Scleral cells ($1\times10^5$ cells/well) were seeded into a 12-well plate. After 24 hours, the original culture medium was replaced with 1 mL conditioned medium. After another 24 hours, the gene expression of scleral cells was measured by real-time polymerase chain reaction (RT-PCR).

8. In Situ Hybridization

The C57BL/6J mice were purchased from the National Laboratory Animal Center, Taiwan. All the animal experiments abided by the ARVO policy for use of animals. After sacrificing the mice, the eyes were collected and fixed in paraformaldehyde (PFA). For in situ hybridization, the eye sections were incubated in imidazole buffer (0.13 M 1-methylimidazole, 300 mM NaCl pH 8.0) twice for 10 minutes, followed by incubation in 1-ethyl-3-(3-dimethylaminopropyl) carbodiimide HCl (EDC; Thermo Fisher Scientific, Rockford, Ill.) solution (16 M EDC, 0.13 M 1-methylimidazole, 300 mM NaCl pH 8.0) for 1 h at 28° C. After twice washing in 0.2% (w/v) glycine/PBS, the sections were acetylated by incubation in 0.1 M triethanolamine, 0.5% (v/v) acetic anhydride for 10 minutes, followed by being washed 3 times in 1×PBS for 5 minutes each wash. 5'-DIG-labeled locked nucleic acid modified microRNA-328 probes (EXIQON, Vedbaek, Denmark) were diluted by a ratio of 1:100 in hybridization buffer (50% formamide, 0.3 M NaCl, 20 mM Tris HCl pH 8.0, 5 mM EDTA, 10 mM $NaPO_4$ pH 8.0, 10% dextran sulfate, 1×Denhardt's solution, and 0.5 mg/mL yeast tRNA) and heated at 65° C. for 5 minutes, then chilled on ice.

After overnight hybridization at 54° C., the slides were washed twice in 50% formamide, 1×SSC-Tween for 25 minutes; once in 0.2×SSC for 15 minutes; once in 1×PBS for 15 minutes. The sections were then incubated in blocking solution (1× Blocking Reagent, Roche) for 1 hour at room temperature, followed by incubation in blocking solution containing a 1:1500 dilution of Alkaline Phosphatase (AP)-conjugated anti-DIG Fab fragment (Roche Applied Science, Indianapolis, USA) for 2 hours at room temperature. The slides were washed twice in 1×PBS-Tween for 20 minutes, then twice in 1×PBS for 20 minutes, and the sections were incubated in BM Purple AP substrate (Roche) for one day in the dark. Alkaline phosphatase substrate reactions were terminated by washing the slides in 1 mM EDTA, 1×PBS for 10 minutes, followed by a 2 minutes wash in deionized water. After mounting, the images were captured under a Nikon inverted microscope (Nikon Instruments Inc.).

9. Statistical Analysis

The Mann-Whitney U test was used to compare all experimental results. A P-value less than 0.05 was considered significant. All the assays shown were conducted in triplicate at least. Data are means±standard deviation of three experiments.

10. Determination of microRNA-328 Expression Level in Sclera and Retina in Myopic Mice A 23-day old young mouse (C57BL/6J mouse, purchased from the National Laboratory Animal Center (Taiwan)) was covered on one eye on one side for four weeks to make the eye develop high myopia, and the un-covered eye of the same mouse was used as a first type of control, and the eyes of another mouse without any covering were used as a second type of control. Determination and/or calculation of expression level in sclera and retina in the mice is described in Method 2.

11. Determination of Whether a Locked Nucleic Acid Modified Antisense for microRNA-328 can Enter into Ocular Tissues In order to determine that a locked nucleic acid modified antisense for microRNA-328 (the sequence thereof was GGAAGGGCAGAGAGGGCCA (SEQ ID NO. 7)) (miRCURY LNA™ microRNA Power inhibitor, Exiqon, Vedbaek, Denmark, catalog number: 427050-00) can enter into ocular tissues in the form of an eye drop, 50 nM locked nucleic acid modified antisense for microRNA-328 was dissolved in PBS buffer while in another experiment group, liposome was used to encapsulate locked nucleic acid modified antisense for microRNA-328. The two medicaments were dropped into different eyes of the mouse, respectively, once a day, for 3 continuous days. On the fourth day, the mouse was sacrificed and in situ hybridization satin experiment was performed. Negative control were the eyes of a normal mouse; for positive control, during the staining, locked nucleic acid modified antisense for microRNA-328 was further added to confirm that the staining process was correct.

B. Results

1. MicroRNA-328 and PAX6

Figure 2B:
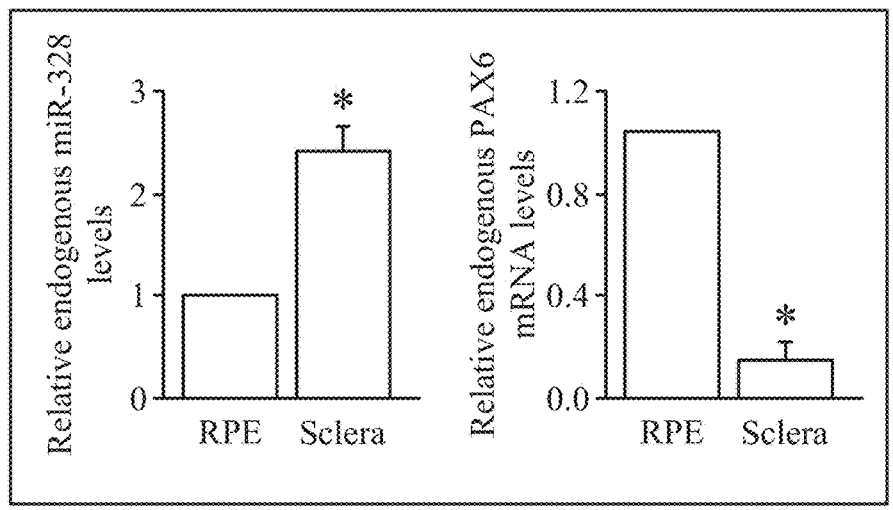
FIG. 2B shows endogenous expression levels of microRNA-328 and PAX6 in retinal pigment epithelium and scleral cells, respectively. The relative levels of microRNA-328 and PAX6 were analyzed by the quantitative polymerase chain reactions.
Figure 2C:
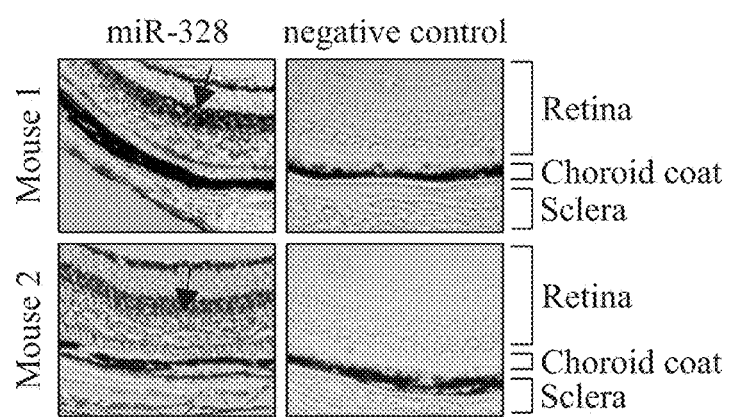
FIG. 2C shows the results of performing in situ hybridization on ocular tissues with locked nucleic acid modified microRNA-328 probes or negative control. Left panel: In situ hybridization of microRNA-328 showed the presence of microRNA-328 in the normal eyes of mice (the position indicated by an arrow mark) (n=2). Right panel: The negative control of in situ hybridization (i.e. without any microRNA-328 probe) did not show any signal.

First, endogenous expression levels of microRNA-328 and PAX6 in retinal pigment epithelium and scleral cells was detected by real-time quantitative polymerase chain reaction analysis. The level of microRNA-328 in retinal pigment epithelium cells was lower than that in scleral cells (FIG. 2B). Conversely, PAX6 expression was higher in retinal pigment epithelium cells than in scleral cells. To test whether microRNA-328 is expressed in vivo, in situ hybridization was performed on murine ocular tissues with LNA-modified microRNA-328 probes. As shown in FIG. 2C, the expression of microRNA-328 can be detected in vivo.

Figure 2D:
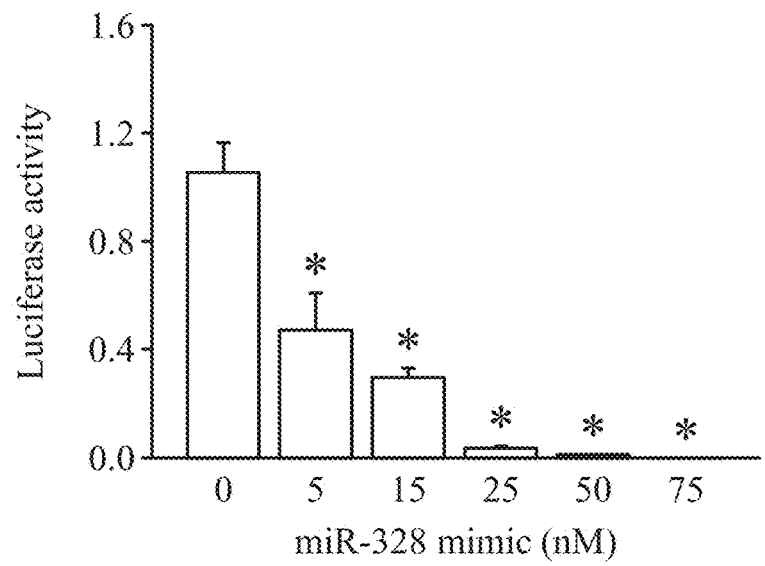
FIGS. 2D and 2E show the results for luciferase assays for microRNA-328 mimic targeting wild-type PAX6 3' untranslated region and mutant PAX6 3' untranslated region, respectively. Cells were transfected with 600 ng pMiR-PAX6 3'UTR or mutant PAX6 3' untranslated region, respectively and dosed with microRNA-328 mimic. After 24 hours, the luciferase activity was measured. pEGFP plasmids were also co-transfected into cells, and the GFP signal was used as an internal control.
Figure 2E:
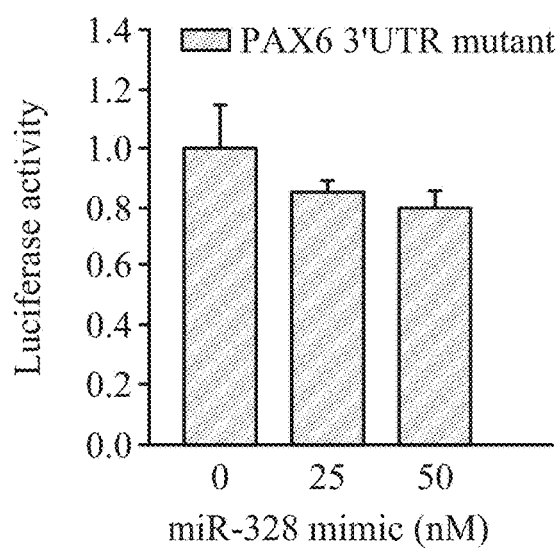

Then, the direct binding between microRNA-328 and PAX6 was validated. A 1500-bp length of PAX6 3' untranslated region containing the putative microRNA-328 binding site was cloned into the pMIR-reporter plasmid. After the pMIR-PAX6 3'UTR plasmid and microRNA-328 mimic were co-transfected into retinal pigment epithelium cells, luciferase activity was measured. As shown in FIG. 2D, microRNA-328 mimic dose-dependently decreased the luciferase activity in retinal pigment epithelium cells. To further validate the binding of PAX6, seven nucleotides located in the critical binding region of the PAX6 3' untranslated region were mutated by site-directed mutagenesis (FIG. 2A). This procedure should reduce or abolish microRNA-328 binding to PAX6. As shown in FIG. 2E, microRNA-328 mimic did not have any effect on luciferase activity after mutating the microRNA-328 target site.

Figure 2F:
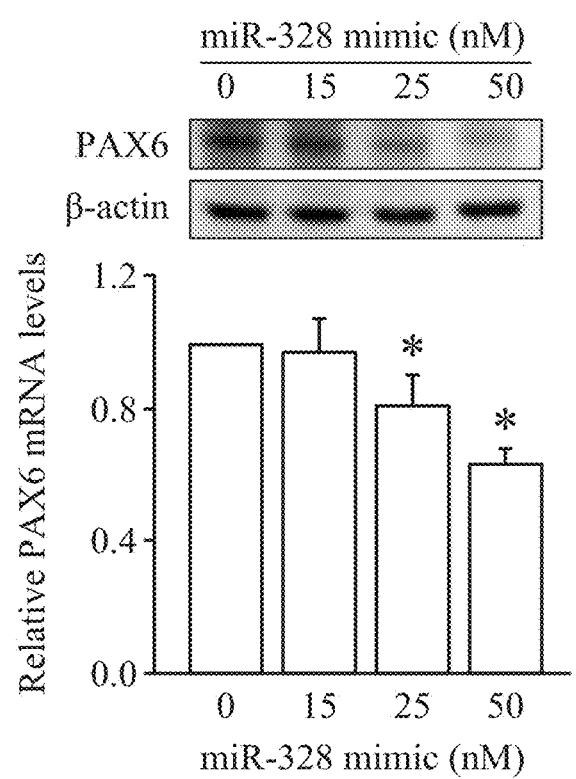
FIG. 2F shows that microRNA-328 mimic decreased PAX6 expression in a dose-dependent manner. After cells were dosed with microRNA-328 mimic for 24 hours, the relative mRNA and protein levels of PAX6 were analyzed by the quantitative polymerase chain reactions and the immunoblotting assays, respectively. Data are means±standard deviation of three experiments, and * means p value<0.05.

Given that the luciferase assay confirmed a direct binding between microRNA-328 and PAX6, whether microRNA-328 can inhibit PAX6 expression in retinal pigment epithelium cells as further tested. After transfecting retinal pigment epithelium cells with different doses of microRNA-328 mimic, PAX6 expression was directly measured. The results showed that microRNA-328 mimic significantly and dose-dependently decreased PAX6 expression (FIG. 2F). The above experiments proved that microRNA-328 negatively regulated PAX6 expression.

Figure 3:
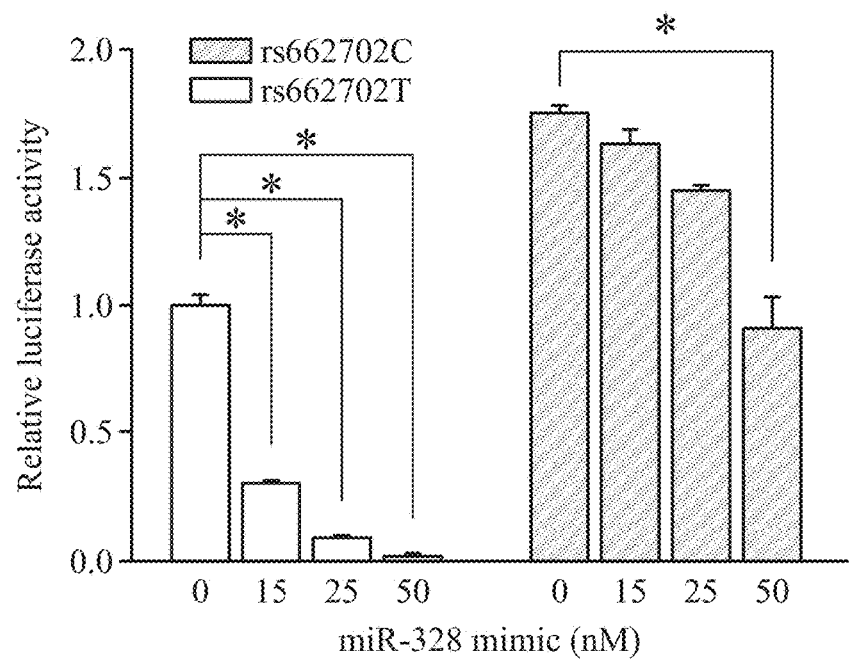
FIG. 3 shows that microRNA-328 binding ability is regulated by PAX6 3' untranslated region SNP rs662702.

2. Single Nucleotide Polymorphism (SNP) Rs662702 Affects microRNA-328 Binding Ability Since single nucleotide polymorphism rs662702 in PAX6 is located in the microRNA-328 binding site, and since this single nucleotide polymorphism was shown to be related to extreme myopia in the recent study of the inventors, whether this SNP can affect microRNA-328 binding ability to the PAX6 3' untranslated region was tested. Two reporter constructs were created: one carried the risk C allele and the other carried the protective T allele. Even a low dose (15 nM) of microRNA-328 mimic could significantly reduce the luciferase activity in retinal pigment epithelium cells transfected with the C-allele constructs (FIG. 3). However, the effect of microRNA-328 mimic was much less on the T-allele constructs than on the C-allele constructs (FIG. 3). Accordingly, 3' untranslated region single nucleotide polymorphism rs662702 substantially affected the binding ability of the microRNA-328 to the PAX6 3' untranslated region, and that might affect PAX6 expression levels and result in myopia formation.

3. Knockdown of PAX6 Enhances Retinal Pigment Epithelium Cell Viability and Regulates TGF-β Expression Loss-of-function experiments were used to investigate PAX6 effects on retinal pigment epithelium cells to more RNA can affect myopia formation by knockdown of PAX6.

First, it was conformed that a short hairpin RNA against PAX6 could knock down PAX6 expressions in a dose-dependent manner in retinal pigment epithelium cells (FIG. 4A). Knockdown of PAX6 significantly enhanced retinal pigment epithelium cell proliferation (FIG. 4B and FIG. 4C). Since previous studies have reported that an increase in TGF-β was an important factor in the retinoscleral signaling pathway during myopia development (J Exp Eye Res 2009; 88:458-466), whether PAX6 affected TGF-β expression in retinal pigment epithelium cells was tested next. The results showed that suppression of PAX6 significantly enhanced TGF-β3 (but not TGF-β1 or TGF-β2) expression in retinal pigment epithelium cells (FIGS. 4D-4F).

To further confirm that PAX6 could mediate TGF-β3 expression in retinal pigment epithelium cells, a gain-of-function experiment was further conducted. The full length (1269 bp; NM_000280) cDNA of PAX6 was cloned into pEGFP-N3 plasmids (FIG. 5A). Retinal pigment epithelium cells would overexpress PAX6 protein. Overexpression of PAX6 significantly inhibited TGF-β3 expression (FIG. 5B). The results indicated that PAX6 may participate in myopia formation through regulating the TGF-β3 mediated signaling pathways.

4. MicroRNA-328 Affects Retinal Pigment Epithelium Viability and TGF-β Expression Since it was confirmed that PAX6 was a microRNA-328 target gene, the effect of microRNA-328 on retinal pigment epithelium proliferation was investigated further. After retinal pigment epithelium cells were transfected with different doses of microRNA-328 mimic for 24 hours, the cell viability and mRNA levels were measured by WST-1 and quantitative polymerase chain reaction assays, respectively. As expected, microRNA-328 mimic dose-dependently enhanced retinal pigment epithelium cell proliferation (FIG. 6A), and this result was similar to the results from short hairpin RNA for PAX6. MicroRNA-328 mimic significantly induced TGF-β3 expression in retinal pigment epithelium cells (FIG. 4B). Furthermore, microRNA-328 mimic did not show significant effects on TGF-β1 and TGF-β2 expression.

5. The Effect of PAX6 on Scleral Cells

Scleral thinning, reduced scleral collagen I accumulation, decreased integrin β1 subunit expression, and increased matrix metalloproteinase 2 (MMP 2) have been reported as scleral phenotypes in the development of myopia (Exp Eye Res 2006; 82:185-200; Invest Ophthalmol Vis Sci 2006; 47:4674-4682; Exp Eye Res 1996; 63:369-381. Invest Ophthalmol Vis Sci 2001; 42:1153-1159; Invest Ophthalmol Vis Sci 2002; 43:2067-2075). Whether a change of PAX6 expression in retinal pigment epithelium cells could affect scleral gene expression was tested. The scleral cells were treated with the conditioned medium, which was collected from retinal pigment epithelium cells with down-regulated PAX6 expression. 24 hours after treatment with the conditioned medium, the cell viability and gene expression level of scleral cells were measured. As shown in FIG. 7A, a dose-dependent decrease of scleral cell viability was found. Furthermore, in scleral cells, it was found that collagen I and integrin β1 levels significantly decreased, but matrix metalloproteinase 2 expression levels increased (FIGS. 7B, 7C, 7D and 7E).

On the contrary, the conditioned medium from the retinal pigment epithelium cells with overexpressed PAX6 had opposite effects on scleral cell proliferation, collagen I, integrin β1, and matrix metalloproteinase 2 expressions (FIGS. 8A, 8B, 8C, 8D and 8E). Therefore, the expression levels of PAX6 in retinal pigment epithelium cells significantly affected the scleral phenotypes.

6. Retinoic Acid Regulates microRNA-328 Expression

Increased retinoic acid (RA) expression has been reported during the development of myopia (Ophthalmic Res 1998; 30:361-367; Vision Res 2004; 44:643-653). However, the role of retinoic acid in myopia development is still not clear. According to the JASPAR database (Nucleic Acids Res 2008; 36:D102-106), some retinoic acid responsive elements are located in the 2 kb promoter region of microRNA-328 gene. Given that retinoic acid was predicted to regulate microRNA-328 expression, retinoic acid-treated retinal pigment epithelium cells could provide a good model to test for the roles of microRNA-328 and PAX6 during myopia formation. After retinal pigment epithelium cells were treated with different doses of retinoic acid for 24 hours, cell viability, RNA and protein levels were measured by WST-1, quantitative polymerase chain reaction and immunoblotting assays, respectively. As shown in FIGS. 9A and 9B, retinoic acid dose-dependently enhanced retinal pigment epithelium cell proliferation. Furthermore, the levels of microRNA-328 in retinal pigment epithelium cells were increased by retinoic acid treatment in a dose-dependent manner (FIG. 9C), and that resulted in a decrease in the expression level of PAX6 (FIG. 9D).

7. Determination of microRNA-328 Expression Level in Sclera and Retina in Myopic Mice In the determination of microRNA-328 expression level in sclera and retina in myopic mice mentioned above, the result found that microRNA-328 has a higher expression level in retina (FIG. 10A) and sclera (FIG. 10B) of the myopic eye than in the eye of the same young mouse and in the eyes of the completely normal mouse.

8. Determination of Whether a Locked Nucleic Acid Modified Antisense for microRNA-328 can Enter into Ocular Tissues In the determination of whether a locked nucleic acid modified antisense for microRNA-328 can enter into ocular tissues, the results for the negative control group (eyes of a normal mouse) and the positive control group (locked nucleic acid modified antisense for microRNA-328 was further added during the staining) are shown in FIG. 11A, and the result for the group treated with locked nucleic acid modified antisense for microRNA-328 is shown in FIG.

11B. According to FIG. 11B, it is known that the location at which locked nucleic acid modified antisense for microRNA-328 located was stained to a purple color (the position indicated by an arrow mark). No matter whether liposome was used to encapsulate or not, it was found that ocular tissues, especially sclera tissue, had a purple color reaction, and that confirmed that locked nucleic acid modified antisense for microRNA-328 could enter into ocular tissues in the form of an eye drop to reach the expected curative effect of treating myopia.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for treating and/or preventing myopia, comprising:
   administering an antisense for microRNA-328 to a subject, wherein the antisense for microRNA-328 is capable of counteracting microRNA-328, and the microRNA-328 is capable of inhibiting an expression of PAX-6 gene, and wherein the sequence of the antisense for microRNA-328 comprises SEQ ID NO. 7, wherein the antisense for microRNA-328 is formulated with a pharmaceutically acceptable carrier to form a medicament, and wherein the medicament is in the form of an eye drop.

2. The method for treating and/or preventing myopia as claimed in claim 1, wherein the antisense for microRNA-328 is composed of non-modified RNA or comprises at least one chemically modified nucleic acid.

3. The method for treating and/or preventing myopia as claimed in claim 2, wherein the chemically modified nucleic acid comprises phosphodiester nucleic acid, phosphorothioate nucleic acid, methylphosphonate nucleic acid, phosphoroamidate nucleic acid, 2'-O-methyl nucleic acid, peptide nucleic acid (PNA), N-Morpholino or locked nucleic acid (LNA).

4. The method for treating and/or preventing myopia as claimed in claim 2, wherein the chemically modified nucleic acid is locked nucleic acid (LNA).

5. The method for treating and/or preventing myopia as claimed in claim 1, wherein the pharmaceutically acceptable carrier comprises a nanoparticle.

6. The method for treating and/or preventing myopia as claimed in claim 5, wherein the nanoparticle comprises a liposome, a micelle, a metal nanoparticle, or a polymer nanoparticle.

7. The method for treating and/or preventing myopia as claimed in claim 5, wherein the nanoparticle is a liposome.

\* \* \* \* \*